(12) United States Patent
Shrivastava et al.

(10) Patent No.: US 9,039,749 B2
(45) Date of Patent: May 26, 2015

(54) METHODS AND APPARATUSES FOR FLOW RESTORATION AND IMPLANTING MEMBERS IN THE HUMAN BODY

(75) Inventors: Sanjay Shrivastava, Irvine, CA (US); Anh Cam, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 500 days.

(21) Appl. No.: 12/896,707

(22) Filed: Oct. 1, 2010

(65) Prior Publication Data

US 2012/0083868 A1 Apr. 5, 2012

(51) Int. Cl.
| | | |
|---|---|---|
| *A61F 2/06* | (2013.01) | |
| *A61B 17/221* | (2006.01) | |
| *A61F 2/86* | (2013.01) | |
| *A61F 2/95* | (2013.01) | |
| A61B 17/22 | (2006.01) | |
| A61F 2/856 | (2013.01) | |

(52) U.S. Cl.
CPC ..... *A61B 17/221* (2013.01); *A61B 2017/22034* (2013.01); *A61B 2017/2215* (2013.01); *A61F 2/856* (2013.01); *A61F 2/86* (2013.01); *A61F 2/95* (2013.01); *A61F 2002/9505* (2013.01); *A61F 2002/9534* (2013.01); *A61F 2210/0076* (2013.01)

(58) Field of Classification Search
CPC ............... A61B 17/221; A61B 2012/12063; A61B 2017/12054; A61B 2017/12059; A61B 2017/12063; A61B 2017/12068; A61F 2220/005; A61F 2220/0025; A61F 2002/9505
USPC ........ 606/191–192, 194, 200; 623/1.11–1.12, 623/1.15–1.17, 1.2, 1.22–1.23, 1.35
See application file for complete search history.

(56) References Cited

U.S. PATENT DOCUMENTS

| | | |
|---|---|---|
| 3,996,938 A | 12/1976 | Clark, III |
| 4,046,150 A | 9/1977 | Schwartz et al. |
| 4,299,255 A | 11/1981 | Miller |
| 4,347,846 A | 9/1982 | Dormia |
| 4,403,612 A | 9/1983 | Fogarty |
| 4,611,594 A | 9/1986 | Grayhack et al. |
| 4,612,931 A | 9/1986 | Dormia |
| 4,650,466 A | 3/1987 | Luther |

(Continued)

FOREIGN PATENT DOCUMENTS

| | | |
|---|---|---|
| BR | 9604566 | 9/1998 |
| CA | 2389374 A1 | 5/2001 |

(Continued)

OTHER PUBLICATIONS

E.I. Levy et al., Self-Expanding Stents for Recanalization of Acute Cerebrovascular Occulsions; AJNR May 28, 2007.

(Continued)

*Primary Examiner* — Darwin Erezo
*Assistant Examiner* — Kendra Obu
(74) *Attorney, Agent, or Firm* — Mark J. Kertz, Esq.

(57) ABSTRACT

A medical device for blood flow restoration and/or for use as an implantable member in a human vessel includes a self-expanding member, a guidewire, and a connection mechanism. The self-expanding member includes a plurality of cells and filaments having specific ranges of thicknesses, widths, and heights. The self-expanding member can take on a volume-reduced coiled form with overlapped edges, and can generate optimal radial forces against a vessel wall and/or thrombus when deployed and expanded.

32 Claims, 16 Drawing Sheets

(56) References Cited

U.S. PATENT DOCUMENTS

| | | |
|---|---|---|
| 4,655,771 A | 4/1987 | Wallsten |
| 4,733,665 A | 3/1988 | Palmaz |
| 4,739,762 A | 4/1988 | Palmaz |
| 4,793,348 A | 12/1988 | Palmaz |
| 4,890,611 A | 1/1990 | Monfort et al. |
| 5,071,407 A | 12/1991 | Termin et al. |
| 5,100,423 A | 3/1992 | Fearnot |
| 5,102,417 A | 4/1992 | Palmaz |
| 5,190,058 A | 3/1993 | Jones et al. |
| 5,192,286 A | 3/1993 | Phan et al. |
| 5,195,984 A | 3/1993 | Schatz |
| 5,197,978 A | 3/1993 | Hess |
| 5,217,484 A * | 6/1993 | Marks .......................... 606/200 |
| 5,222,971 A | 6/1993 | Willard et al. |
| 5,330,482 A | 7/1994 | Gibbs et al. |
| 5,354,295 A | 10/1994 | Guglielmi et al. |
| 5,411,549 A | 5/1995 | Peters |
| 5,423,829 A | 6/1995 | Pham et al. |
| 5,456,667 A | 10/1995 | Ham et al. |
| 5,490,859 A | 2/1996 | Mische et al. |
| 5,496,330 A | 3/1996 | Bates et al. |
| 5,501,694 A | 3/1996 | Ressemann et al. |
| 5,527,326 A | 6/1996 | Hermann et al. |
| 5,540,680 A | 7/1996 | Guglielmi et al. |
| 5,540,707 A | 7/1996 | Ressemann et al. |
| 5,569,245 A | 10/1996 | Guglielmi et al. |
| 5,571,122 A | 11/1996 | Kelly et al. |
| 5,573,520 A | 11/1996 | Schwartz et al. |
| 5,624,449 A | 4/1997 | Pham et al. |
| 5,669,933 A | 9/1997 | Simon et al. |
| 5,690,667 A | 11/1997 | Gia |
| 5,695,519 A | 12/1997 | Summers et al. |
| 5,720,764 A | 2/1998 | Naderlinger |
| 5,743,905 A | 4/1998 | Eder et al. |
| 5,749,883 A | 5/1998 | Halpern |
| 5,759,192 A | 6/1998 | Saunders |
| 5,769,882 A | 6/1998 | Fogarty et al. |
| 5,792,145 A | 8/1998 | Bates et al. |
| 5,792,157 A | 8/1998 | Mische et al. |
| 5,800,454 A | 9/1998 | Jacobsen et al. |
| 5,800,520 A | 9/1998 | Fogarty et al. |
| 5,800,525 A | 9/1998 | Bachinski et al. |
| 5,814,064 A | 9/1998 | Daniel et al. |
| 5,824,037 A | 10/1998 | Fogarty et al. |
| 5,827,304 A | 10/1998 | Hart |
| 5,836,868 A | 11/1998 | Ressemann et al. |
| 5,848,964 A | 12/1998 | Samuels |
| 5,851,206 A | 12/1998 | Guglielmi et al. |
| 5,855,578 A | 1/1999 | Guglielmi et al. |
| 5,882,329 A | 3/1999 | Patterson et al. |
| 5,891,128 A | 4/1999 | Gia et al. |
| 5,895,385 A | 4/1999 | Guglielmi et al. |
| 5,895,398 A | 4/1999 | Wensel et al. |
| 5,897,567 A | 4/1999 | Ressemann et al. |
| 5,904,698 A | 5/1999 | Thomas et al. |
| 5,911,717 A | 6/1999 | Jacobsen et al. |
| 5,911,734 A | 6/1999 | Tsugita et al. |
| 5,913,895 A | 6/1999 | Burpee et al. |
| 5,916,235 A | 6/1999 | Guglielmi |
| 5,919,187 A | 7/1999 | Guglielmi et al. |
| 5,925,037 A | 7/1999 | Guglielmi et al. |
| 5,925,061 A | 7/1999 | Ogi et al. |
| 5,928,226 A | 7/1999 | Guglielmi et al. |
| 5,935,139 A | 8/1999 | Bates |
| 5,941,869 A | 8/1999 | Patterson et al. |
| 5,944,714 A | 8/1999 | Guglielmi et al. |
| 5,947,962 A | 9/1999 | Guglielmi et al. |
| 5,947,995 A | 9/1999 | Samuels |
| 5,948,016 A | 9/1999 | Jang |
| 5,954,743 A | 9/1999 | Jang |
| 5,964,797 A | 10/1999 | Ho |
| 5,972,019 A | 10/1999 | Engelson et al. |
| 5,976,126 A | 11/1999 | Guglielmi |
| 5,976,131 A | 11/1999 | Guglielmi et al. |
| 5,980,514 A | 11/1999 | Kupiecki et al. |
| 5,984,929 A | 11/1999 | Bashiri et al. |
| 6,010,498 A | 1/2000 | Guglielmi |
| 6,013,093 A | 1/2000 | Nott et al. |
| 6,039,721 A | 3/2000 | Johnson et al. |
| 6,063,100 A | 5/2000 | Diaz et al. |
| 6,063,111 A | 5/2000 | Hieshima et al. |
| 6,066,149 A | 5/2000 | Samson et al. |
| 6,066,158 A | 5/2000 | Engelson et al. |
| 6,077,260 A | 6/2000 | Wheelock et al. |
| 6,083,220 A | 7/2000 | Guglielmi et al. |
| 6,096,034 A | 8/2000 | Kupiecki et al. |
| 6,096,053 A | 8/2000 | Bates |
| 6,099,549 A | 8/2000 | Bosma et al. |
| 6,110,198 A | 8/2000 | Fogarty et al. |
| 6,118,001 A | 9/2000 | Owen et al. |
| 6,123,714 A | 9/2000 | Gia et al. |
| 6,129,755 A | 10/2000 | Mathis et al. |
| 6,146,396 A | 11/2000 | Konya et al. |
| 6,156,061 A | 12/2000 | Wallace et al. |
| 6,165,178 A | 12/2000 | Bashiri et al. |
| 6,165,213 A | 12/2000 | Goicoechea et al. |
| 6,168,592 B1 | 1/2001 | Kupiecki et al. |
| 6,168,603 B1 | 1/2001 | Leslie et al. |
| 6,179,857 B1 | 1/2001 | Diaz et al. |
| 6,187,017 B1 | 2/2001 | Gregory, Jr. |
| 6,190,394 B1 | 2/2001 | Lind et al. |
| 6,193,745 B1 | 2/2001 | Fogarty et al. |
| 6,203,552 B1 | 3/2001 | Bagley et al. |
| 6,214,025 B1 | 4/2001 | Thistle et al. |
| 6,238,412 B1 | 5/2001 | Dubrul et al. |
| 6,241,746 B1 | 6/2001 | Bosma et al. |
| 6,245,089 B1 | 6/2001 | Daniel et al. |
| 6,254,571 B1 | 7/2001 | Hart |
| 6,254,628 B1 | 7/2001 | Wallace et al. |
| 6,264,686 B1 | 7/2001 | Rieu et al. |
| 6,264,687 B1 | 7/2001 | Tomonto |
| 6,267,777 B1 | 7/2001 | Bosma et al. |
| 6,273,900 B1 | 8/2001 | Nott et al. |
| 6,277,125 B1 | 8/2001 | Barry et al. |
| 6,277,126 B1 | 8/2001 | Barry et al. |
| 6,306,141 B1 | 10/2001 | Jervis |
| 6,312,463 B1 | 11/2001 | Rourke et al. |
| 6,325,815 B1 | 12/2001 | Kusleika et al. |
| 6,336,934 B1 | 1/2002 | Gilson et al. |
| 6,344,041 B1 | 2/2002 | Kupiecki et al. |
| 6,361,558 B1 | 3/2002 | Hieshima et al. |
| 6,371,969 B1 | 4/2002 | Tsugita et al. |
| 6,379,329 B1 | 4/2002 | Naglreiter et al. |
| 6,383,205 B1 | 5/2002 | Samson et al. |
| 6,402,771 B1 | 6/2002 | Palmer et al. |
| 6,409,721 B1 | 6/2002 | Wheelock et al. |
| 6,425,893 B1 | 7/2002 | Guglielmi |
| 6,425,914 B1 | 7/2002 | Wallace et al. |
| 6,428,558 B1 | 8/2002 | Jones et al. |
| 6,432,122 B1 | 8/2002 | Gilson et al. |
| 6,443,971 B1 | 9/2002 | Boylan et al. |
| 6,443,972 B1 | 9/2002 | Bosma et al. |
| 6,458,139 B1 | 10/2002 | Palmer et al. |
| 6,468,266 B1 | 10/2002 | Bashiri et al. |
| 6,485,524 B2 | 11/2002 | Strecker |
| 6,491,719 B1 | 12/2002 | Fogarty et al. |
| 6,500,182 B2 | 12/2002 | Foster |
| 6,514,273 B1 | 2/2003 | Voss et al. |
| 6,520,968 B2 | 2/2003 | Bates et al. |
| 6,530,935 B2 | 3/2003 | Wensel et al. |
| 6,533,811 B1 | 3/2003 | Ryan et al. |
| 6,551,342 B1 | 4/2003 | Shen et al. |
| 6,554,849 B1 | 4/2003 | Jones et al. |
| 6,572,648 B1 | 6/2003 | Klumb et al. |
| 6,575,997 B1 | 6/2003 | Palmer et al. |
| 6,589,230 B2 | 7/2003 | Gia et al. |
| 6,589,236 B2 | 7/2003 | Wheelock et al. |
| 6,592,607 B1 | 7/2003 | Palmer et al. |
| 6,620,152 B2 | 9/2003 | Guglielmi |
| 6,641,590 B1 | 11/2003 | Palmer et al. |
| 6,645,224 B2 | 11/2003 | Gilson et al. |
| 6,652,548 B2 | 11/2003 | Evans et al. |
| 6,656,214 B1 | 12/2003 | Fogarty et al. |
| 6,660,014 B2 | 12/2003 | Demarais et al. |

(56) References Cited

U.S. PATENT DOCUMENTS

| | | | |
|---|---|---|---|
| 6,660,021 | B1 | 12/2003 | Palmer et al. |
| 6,663,650 | B2 | 12/2003 | Sepetka et al. |
| 6,673,106 | B2 | 1/2004 | Mitelberg et al. |
| 6,679,893 | B1 | 1/2004 | Tran |
| 6,692,508 | B2 | 2/2004 | Wensel et al. |
| 6,702,782 | B2 | 3/2004 | Miller et al. |
| 6,702,843 | B1 | 3/2004 | Brown et al. |
| 6,716,238 | B2 | 4/2004 | Elliott |
| 6,723,108 | B1 | 4/2004 | Jones et al. |
| 6,743,236 | B2 | 6/2004 | Barry et al. |
| 6,811,560 | B2 | 11/2004 | Jones et al. |
| 6,818,013 | B2 | 11/2004 | Mitelberg et al. |
| 6,833,002 | B2 | 12/2004 | Stack et al. |
| 6,833,003 | B2 | 12/2004 | Jones et al. |
| 6,878,151 | B2 | 4/2005 | Carrison et al. |
| 6,887,268 | B2 | 5/2005 | Butaric et al. |
| 6,893,413 | B2 | 5/2005 | Martin |
| 6,913,612 | B2 | 7/2005 | Palmer et al. |
| 6,921,414 | B2 | 7/2005 | Klumb et al. |
| 6,945,977 | B2 | 9/2005 | Demarais et al. |
| 6,953,468 | B2 | 10/2005 | Jones et al. |
| 6,955,685 | B2 | 10/2005 | Escamilla et al. |
| 6,960,227 | B2 | 11/2005 | Jones et al. |
| 6,960,228 | B2 | 11/2005 | Mitelberg et al. |
| 6,974,473 | B2 | 12/2005 | Barclay et al. |
| 6,989,020 | B2 | 1/2006 | Jones et al. |
| 7,001,422 | B2 | 2/2006 | Escamilla et al. |
| 7,004,954 | B1 | 2/2006 | Voss et al. |
| 7,004,956 | B2 | 2/2006 | Palmer et al. |
| 7,037,331 | B2 | 5/2006 | Mitelberg et al. |
| 7,041,116 | B2 | 5/2006 | Goto et al. |
| 7,052,500 | B2 | 5/2006 | Bashiri et al. |
| 7,058,456 | B2 | 6/2006 | Pierce |
| 7,101,380 | B2 | 9/2006 | Khachin et al. |
| 7,128,073 | B1 | 10/2006 | van der Burg et al. |
| 7,147,659 | B2 | 12/2006 | Jones |
| 7,156,871 | B2 | 1/2007 | Jones et al. |
| 7,172,617 | B2 | 2/2007 | Colgan et al. |
| 7,179,273 | B1 | 2/2007 | Palmer et al. |
| 7,179,276 | B2 | 2/2007 | Barry et al. |
| 7,182,774 | B2 | 2/2007 | Barry et al. |
| 7,195,648 | B2 | 3/2007 | Jones et al. |
| 7,201,769 | B2 | 4/2007 | Jones et al. |
| 7,232,432 | B2 | 6/2007 | Fulton, III et al. |
| 7,264,628 | B2 | 9/2007 | Jones et al. |
| 7,270,674 | B2 | 9/2007 | Jones et al. |
| 7,285,126 | B2 | 10/2007 | Sepetka et al. |
| 7,294,123 | B2 | 11/2007 | Jones et al. |
| 7,300,458 | B2 | 11/2007 | Henkes et al. |
| 7,306,622 | B2 | 12/2007 | Jones et al. |
| 7,309,351 | B2 | 12/2007 | Escamilla et al. |
| 7,311,726 | B2 | 12/2007 | Mitelberg et al. |
| 7,323,000 | B2 | 1/2008 | Monstdt et al. |
| 7,344,550 | B2 | 3/2008 | Carrison et al. |
| 7,344,558 | B2 | 3/2008 | Lorenzo et al. |
| 7,351,255 | B2 | 4/2008 | Andreas |
| 7,357,809 | B2 | 4/2008 | Jones et al. |
| 7,367,987 | B2 | 5/2008 | Balgobin et al. |
| 7,371,251 | B2 | 5/2008 | Mitelberg et al. |
| 7,371,252 | B2 | 5/2008 | Balgobin et al. |
| 7,377,932 | B2 | 5/2008 | Mitelberg et al. |
| 7,481,821 | B2 | 1/2009 | Fogarty et al. |
| 7,485,122 | B2 * | 2/2009 | Teoh ............................ 606/108 |
| 7,510,565 | B2 | 3/2009 | Gilson et al. |
| 7,517,352 | B2 | 4/2009 | Evans et al. |
| 7,524,319 | B2 | 4/2009 | Dubrul |
| 7,534,252 | B2 | 5/2009 | Sepetka et al. |
| 7,549,974 | B2 | 6/2009 | Nayak |
| 7,553,314 | B2 | 6/2009 | Khachin et al. |
| 7,553,321 | B2 | 6/2009 | Litzenberg et al. |
| 7,582,101 | B2 | 9/2009 | Jones et al. |
| 7,780,694 | B2 | 8/2010 | Palmer et al. |
| 7,833,240 | B2 | 11/2010 | Okushi et al. |
| 8,052,640 | B2 | 11/2011 | Fiorella et al. |
| 8,062,307 | B2 | 11/2011 | Sepetka et al. |
| 8,066,757 | B2 | 11/2011 | Ferrera et al. |
| 8,070,791 | B2 | 12/2011 | Ferrera et al. |
| 8,100,935 | B2 | 1/2012 | Rosenbluth et al. |
| 8,105,333 | B2 | 1/2012 | Sepetka et al. |
| 8,197,493 | B2 * | 6/2012 | Ferrera et al. .................. 606/127 |
| 8,357,179 | B2 * | 1/2013 | Grandfield et al. ............ 606/200 |
| 2001/0003801 | A1 | 6/2001 | Strecker |
| 2001/0041899 | A1 | 11/2001 | Foster |
| 2001/0044649 | A1 | 11/2001 | Vallana et al. |
| 2001/0053929 | A1 | 12/2001 | Vonesh et al. |
| 2002/0193868 | A1 | 12/2002 | Mitelberg et al. |
| 2003/0153944 | A1 | 8/2003 | Phung et al. |
| 2004/0059407 | A1 | 3/2004 | Escamilla et al. |
| 2004/0078050 | A1 | 4/2004 | Monstadt et al. |
| 2004/0098025 | A1 | 5/2004 | Sepetka et al. |
| 2005/0021125 | A1 | 1/2005 | Stack et al. |
| 2005/0033348 | A1 | 2/2005 | Sepetka et al. |
| 2005/0165441 | A1 | 7/2005 | McGuckin et al. |
| 2005/0209678 | A1 | 9/2005 | Henkes et al. |
| 2005/0222676 | A1 | 10/2005 | Shanley et al. |
| 2006/0085065 | A1 | 4/2006 | Krause et al. |
| 2006/0195118 | A1 | 8/2006 | Richardson |
| 2006/0224179 | A1 | 10/2006 | Kucharczyk et al. |
| 2007/0179513 | A1 | 8/2007 | Deutsch |
| 2007/0185501 | A1 | 8/2007 | Martin et al. |
| 2007/0198029 | A1 | 8/2007 | Martin et al. |
| 2007/0208367 | A1 | 9/2007 | Fiorella et al. |
| 2007/0208371 | A1 | 9/2007 | French et al. |
| 2007/0225749 | A1 | 9/2007 | Martin et al. |
| 2007/0266542 | A1 | 11/2007 | Melsheimer |
| 2007/0288038 | A1 | 12/2007 | Bimbo |
| 2008/0082107 | A1 | 4/2008 | Miller et al. |
| 2008/0119888 | A1 | 5/2008 | Huffmaster |
| 2008/0125855 | A1 | 5/2008 | Henkes et al. |
| 2008/0183185 | A1 | 7/2008 | Miller et al. |
| 2008/0183198 | A1 | 7/2008 | Sepetka et al. |
| 2008/0188865 | A1 | 8/2008 | Miller et al. |
| 2008/0269774 | A1 | 10/2008 | Garcia et al. |
| 2009/0069828 | A1 | 3/2009 | Martin et al. |
| 2009/0163851 | A1 | 6/2009 | Holloway et al. |
| 2009/0275974 | A1 * | 11/2009 | Marchand et al. ............ 606/194 |
| 2010/0042133 | A1 * | 2/2010 | Ramzipoor et al. .......... 606/191 |
| 2010/0174309 | A1 | 7/2010 | Fulkerson et al. |
| 2011/0060212 | A1 | 3/2011 | Slee et al. |

FOREIGN PATENT DOCUMENTS

| | | |
|---|---|---|
| DE | 2804058 A1 | 8/1978 |
| DE | 2821048 B1 | 11/1979 |
| DE | 8435489 U1 | 8/1986 |
| DE | 19703482 A1 | 8/1998 |
| DE | 10010840 A1 | 9/2001 |
| EP | 201466 A2 | 11/1986 |
| EP | 484468 A1 | 5/1992 |
| EP | 629125 A1 | 12/1994 |
| EP | 707830 A1 | 4/1996 |
| EP | 719522 A1 | 7/1996 |
| EP | 726745 A1 | 8/1996 |
| EP | 737450 A1 | 10/1996 |
| EP | 739606 A1 | 10/1996 |
| EP | 750886 A1 | 1/1997 |
| EP | 752236 A1 | 1/1997 |
| EP | 800790 A2 | 10/1997 |
| EP | 803230 A2 | 10/1997 |
| EP | 804904 A1 | 11/1997 |
| EP | 804905 A1 | 11/1997 |
| EP | 804906 A2 | 11/1997 |
| EP | 807410 A2 | 11/1997 |
| EP | 820729 A1 | 1/1998 |
| EP | 826341 A1 | 3/1998 |
| EP | 826342 A1 | 3/1998 |
| EP | 832606 A1 | 4/1998 |
| EP | 861634 A2 | 9/1998 |
| EP | 914803 A1 | 5/1999 |
| EP | 964659 A1 | 12/1999 |
| EP | 1005837 A2 | 6/2000 |
| EP | 1009295 A1 | 6/2000 |
| EP | 1009296 A1 | 6/2000 |
| EP | 1225844 A2 | 7/2002 |

(56) References Cited

FOREIGN PATENT DOCUMENTS

| | | |
|---|---|---|
| EP | 1266639 A2 | 12/2002 |
| EP | 1266640 A2 | 12/2002 |
| EP | 1323385 A2 | 7/2003 |
| EP | 1329196 A1 | 7/2003 |
| EP | 1351626 A2 | 10/2003 |
| EP | 1366720 A1 | 12/2003 |
| EP | 1400219 A1 | 3/2004 |
| FR | 2343488 A1 | 10/1977 |
| GB | 2020557 A | 11/1979 |
| JP | 2-95359 A | 4/1990 |
| JP | 02255157 A | 10/1990 |
| JP | 6-246004 | 9/1994 |
| JP | 8-033719 A | 2/1996 |
| JP | 2975584 B2 | 11/1999 |
| JP | 2001-190686 A | 7/2001 |
| JP | 2001178830 A | 7/2001 |
| WO | WO-9617634 A2 | 6/1996 |
| WO | WO-9628116 A2 | 9/1996 |
| WO | WO-97/04711 A1 | 2/1997 |
| WO | WO-98/25656 A2 | 6/1998 |
| WO | WO-9855175 A1 | 12/1998 |
| WO | WO-9916382 A2 | 4/1999 |
| WO | WO-9923976 A1 | 5/1999 |
| WO | WO-9925252 A1 | 5/1999 |
| WO | WO-9929264 A1 | 6/1999 |
| WO | WO-9944542 A2 | 9/1999 |
| WO | WO-9948429 A1 | 9/1999 |
| WO | WO-9948440 A1 | 9/1999 |
| WO | WO-0012166 A1 | 3/2000 |
| WO | WO-00/59405 A1 | 10/2000 |
| WO | WO-0132099 A2 | 5/2001 |
| WO | WO-0145566 A1 | 6/2001 |
| WO | WO-0172240 A1 | 10/2001 |
| WO | WO-01/93780 A2 | 12/2001 |
| WO | WO-02054980 A2 | 7/2002 |
| WO | WO-2004008991 A1 | 1/2004 |
| WO | WO-2008063156 A2 | 5/2008 |
| WO | WO-2009105710 | 8/2009 |

OTHER PUBLICATIONS

Schumacher, H., "Endovascular Mechanical Thrombectomy of an Occluded Superior Division Branch of the Left MCA for Acute Cardioembolic Stroke," Cardiovascular and Interventional Radiology, Jun. 2003 26(3) pp. 305-308.

Nesbit, G., "New and Future Endovascular Treatment Strategies for Acute Ischemic Stroke," Journal of Vascular and Interventional Radiology, Jan. 2004 15(1) pp. S103-S110.

Imai, K., "Clot Removal Therapy by Aspiration and Extraction for Acute Embolic Carotid Occlusion," American Journal of Neuroradiology, Aug. 2006, vol. 27, pp. 1521-1527.

Wildberger, J., "Percutaneous Venous Thrombectomy Using the Arrow-Trerotola Percutaneous Thrombolytic Device (PTD) with Temporary Caval Filtration: In Vitro Investigations," Cardiovascular and Interventional Radiology, Mar. 2005 28(2) pp. 221-227.

Castano, C., "Use of the New Solitaire (TM) AB Device for Mechanical Thrombectomy when Merci Clot Retriever Has Failed to Remove the Clot. A Case Report.," Interventional Neuroradiology, Jul. 2009 15(2) pp. 209-214.

ev3 Solitaire Brochure R2 dated Jan. 12, 2009.

ev3 Solitaire AB Instructions for Use (IFU) dated Dec. 2007. The first commercial sale of the products numbered SAB-4-15 and SAB 4 20, referenced in the ev3 Solitaire AB IFU dated Dec. 2007 occurred on Jan. 4, 2008.

U.S. Appl. No. 60/987,384, filed Nov. 12, 2007.

Henkes, H., et al., "A Novel Microcatheter-Delivered, Highly-Flexible and Fully-Retrievable Stent, Specifically Designed for Intracranial Use", Interventional Neuroradiolog, vol. 9, pp. 391-393, 2003.

US 6,056,761, 05/2000, Gia et al. (withdrawn)

\* cited by examiner

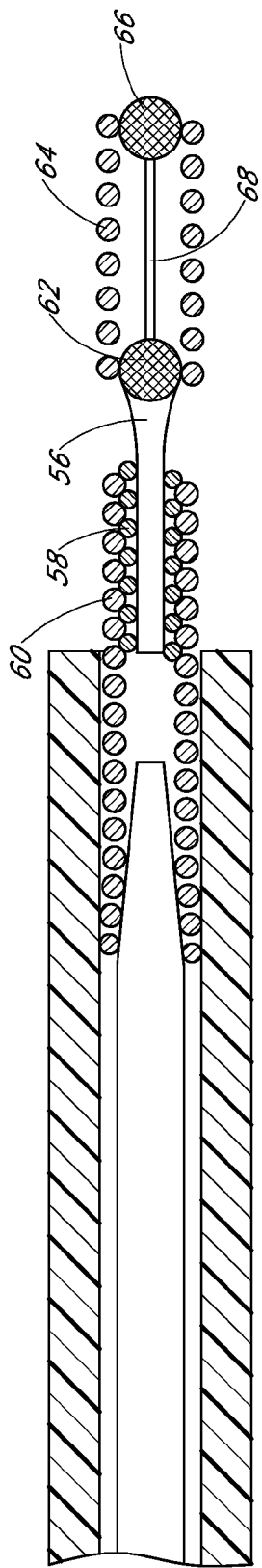
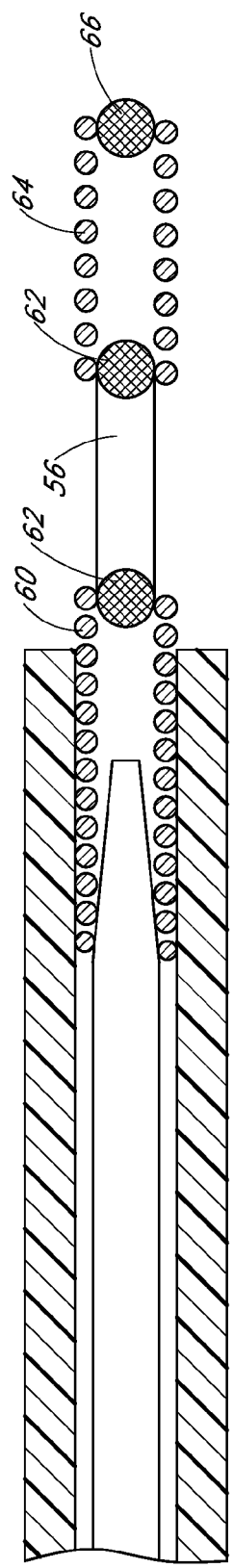
FIG. 8B
FIG. 8C

METHODS AND APPARATUSES FOR FLOW RESTORATION AND IMPLANTING MEMBERS IN THE HUMAN BODY

FIELD OF THE INVENTIONS

The present application relates to methods and apparatuses for restoring at least partial blood flow in occluded blood vessels, particularly occluded cerebral arteries, and to the application of such apparatuses for thrombus removal and/or thrombus dissolution. The present application also relates to using such apparatuses as implantable members in the human body.

BACKGROUND

Occluded blood vessels can be caused by a blood clot (i.e. thrombus) that forms in the blood vessel or by a blood clot that travels downstream (i.e. embolus). The blockage disrupts blood flow, which prevents oxygen and nutrients from being delivered to their intended locations. Tissue distal of a blood clot that is deprived of oxygen and nutrients can no longer function properly. For every minute that treatment is delayed, additional cellular death of critical tissue can occur.

Current technology for blood flow restoration, for example for treating cerebral arteries occluded by thrombi, can often take hours to reestablish flow in the artery, and can lead to unintended complications. Apparatuses and methods for treating cerebral thrombi are often ineffective or only partially effective at resolving thrombus removal, and may result in distal embolization or embolization of uninvolved arteries. For example, some current devices are designed to pierce through a thrombus, or are designed to deploy completely distal of the thrombus before engaging the thrombus. These devices can often fail to capture all of a thrombus, can damage vessel walls distal of a thrombus, can be difficult to maneuver, can unintentionally dislodge portions of a thrombus prior to capture, and/or can take significant amounts of time to restore blood flow.

Additional treatment options include endovascular therapy and/or pharmacological agents. Pharmacological agents, specifically thrombolytics, can be used to dissolve a thrombus and restore blood flow. However, these drugs often do not work in recanalizing the vessel, may not be suitable for some patients, and may take an extended length of time to work, which can impact the cellular death distal of the thrombus. Often these drugs are used within a short treatment window and those patients late in presentation will not be eligible for drug treatment. Also, these drugs can increase the risk to patients for incidences of hemorrhage.

Current technology for implantable members, for example stents for treating vasoconstriction or for closing off vessel wall ballooning in aneurysms or fistulae (e.g. aneurysm bridging devices), is also known. Balloon dilatable stents, for example, are commonly used to treat vasoconstriction or aneurysms. These balloon dilatable stents are often crimped over a non-expanded balloon in a non-dilated state, moved to the treatment location by means of a catheter system and then, by expanding the balloon, dilated and thus anchored within the vessel. Other devices include, for example, stents made of shape-memory material that possess a braid-like structure and are initially introduced and moved in a collapsed state through a catheter to the destination site where they expand either due to temperature changes or because the mechanical force exerted by the catheter is no longer effective.

SUMMARY

An aspect of at least one of the embodiments described herein includes the realization that it would be advantageous to have a device that can be used both as a blood flow restoration device and as a device for use as an implantable member.

Another aspect of at least one of the embodiments described herein includes the realization that during blood flow restoration and/or during placement of an implantable member, it is often difficult to accurately place and position a blood flow restoration device and/or implantable member. Therefore, it would be advantageous to have an apparatus for blood flow restoration and/or for use as an implantable member that can quickly and easily be repositioned, relocated, and/or retrieved within a vessel.

Another aspect of at least one of the embodiments described herein includes the realization that thrombi in a vessel can often be generally soft in nature (e.g. easily malleable) or hard (e.g. callous). Many current blood flow restoration devices are capable of at least partially engaging and/or removing hard thrombi, but do not work well for soft thrombi, and vice versa. Therefore it would be advantageous to have an apparatus for blood flow restoration that is capable of efficiently engaging and removing both soft and hard thrombi.

Another aspect of at least one of the embodiments described herein includes the realization that many current blood flow restoration devices are comprised of meshes that have cell sizes that drastically change in shape and size during expansion and contraction of the device. Such changes in shape and size can make it difficult to retain and hold onto a thrombus, and can lead to unintended additional clots (i.e. emboli) downstream of a thrombus. Therefore, it would be advantageous to have an apparatus for blood flow restoration that is capable of efficiently engaging and removing a thrombus without substantially losing a grip on the thrombus.

Another aspect of at least one of the embodiments described herein includes the realization that many current blood flow restoration devices require the device to initially pierce through the thrombus prior to removal of the thrombus, thereby sometimes leading to untended damage to the vessel, unintended movement of the clot, incomplete clot retention and removal, and/or delay in creating flow restoration. It would be advantageous to have an apparatus for blood flow restoration that can engage and/or remove a thrombus from the side, and immediately restore at least partial blood flow upon expansion.

Another aspect of at least one of the embodiments described herein includes the realization that thrombi are often located at bifurcations, bi-vessels, and/or multi-vessel within the human body. It would be advantageous to have an apparatus for blood flow restoration that is capable of restoring blood flow at a bifurcation, bi-vessel, and/or multi-vessel, and/or removing a thrombus.

Another aspect of at least one of the embodiments described herein includes the realization that many current devices for blood flow restoration and/or for use as an implantable member are often difficult to maneuver within a microcatheter, and require specialized deployment mechanisms. It would be advantageous to have an apparatus for blood flow restoration and/or for use as an implantable member that can quickly and easily be moved through and deployed out a distal end of a traditional microcatheter without the need for a specialized deployment system.

Thus, in accordance with at least one embodiment, a medical device can comprise a guidewire having a proximal end and a distal end, a connection mechanism, and a self-expanding member attached to the distal end of the guidewire via the connection mechanism. The self-expanding member can have a mesh configuration and comprise a proximal portion having a first plurality of cells, the proximal portion being tapered along a longitudinal portion of its length, a distal portion having a second plurality of cells, the distal portion forming a generally tube-like configuration having a central, longitudinal axis, and a seam along a longitudinal axis of the distal portion, the seam forming two edges extending generally longitudinally along the self-expanding member. The self-expanding member can be modified into a volume-reduced form having a generally coiled, tubular configuration for insertion within a microcatheter, the edges of the distal portion being overlapped in the volume-reduced coiled configuration such that in the volume-reduced coiled configuration the self-expanding member has multiple layers in at least one radial direction. A distal end of the distal portion can further comprise filaments that include distal elements, the filaments and distal elements of the distal end being bent radially inwardly towards the central longitudinal axis. The first plurality of cells can comprise filaments having a filament thickness of between 0.045 mm and 0.080 mm, and a filament width of between 0.040 mm and 0.090 mm. The second plurality of cells can comprise filaments having a filament thickness of between 0.040 mm and 0.075 mm, and a filament width of between 0.038 mm and 0.082 mm. The second plurality of cells can comprise cells having a width of between 3.50 mm to 5.50 mm and a height of between 2.50 mm to 4.5 mm. The self-expanding member can have a radial force measurement greater than or equal to 0.0010 N/mm and a chronic outward force of less than or equal to 0.026 N/mm as measured using a thin film method of testing, and a radial force measurement of between approximately 6 to 37 gf/in as measured using a two-pin method of testing.

In accordance with another embodiment, a medical device can comprise a guidewire having a proximal end and a distal end, a connection mechanism, and a self-expanding member attached to the distal end of the guidewire via the connection mechanism. The self-expanding member can have a mesh configuration and comprise a proximal portion having a first plurality of cells, the proximal portion being tapered along a longitudinal portion of its length, a distal portion having a second plurality of cells, the distal portion forming a generally tube-like configuration having a central, longitudinal axis, and a seam along a longitudinal axis of the distal portion, the seam forming two edges extending generally longitudinally along the self-expanding member. The self-expanding member can be modified into a volume-reduced form having a generally coiled, tubular configuration for insertion within a microcatheter, the edges of the distal portion being overlapped in the volume-reduced coiled configuration such that in the volume-reduced coiled configuration the self-expanding member has multiple layers in at least one radial direction. A distal end of the distal portion can further comprise filaments that include a plurality of distal elements, the filaments of the distal end being bent radially inwardly towards the central longitudinal axis.

In accordance with another embodiment, a medical device can comprise a guidewire having a proximal end and a distal end, a connection mechanism, and a self-expanding member attached to the distal end of the guidewire via the connection mechanism. The self-expanding member can have a mesh configuration and comprise a proximal portion having a first plurality of cells, the proximal portion being tapered along a longitudinal portion of its length, a distal portion having a second plurality of cells, the distal portion forming a generally tube-like configuration having a central, longitudinal axis, and a seam along a longitudinal axis of the distal portion, the seam forming two edges extending generally longitudinally along the self-expanding member. The self-expanding member can be modified into a volume-reduced form having a generally coiled, tubular configuration for insertion within a microcatheter, the edges of the distal portion being overlapped in the volume-reduced coiled configuration such that in the volume-reduced coiled configuration the self-expanding member has multiple layers in at least one radial direction. The first plurality of cells can comprise filaments having a filament thickness of between 0.045 mm and 0.080 mm, and a filament width of between 0.040 mm and 0.090 mm. The second plurality of cells can comprise filaments having a filament thickness of between 0.040 mm and 0.075 mm, and a filament width of between 0.038 mm and 0.082 mm.

In accordance with another embodiment, a medical device can comprise a guidewire having a proximal end and a distal end, a connection mechanism, and a self-expanding member attached to the distal end of the guidewire via the connection mechanism. The self-expanding member can have a mesh configuration and comprise a proximal portion having a first plurality of cells, the proximal portion being tapered along a longitudinal portion of its length, a distal portion having a second plurality of cells, the distal portion forming a generally tube-like configuration having a central, longitudinal axis, and a seam along a longitudinal axis of the distal portion, the seam forming two edges extending generally longitudinally along the self-expanding member. The self-expanding member can be modified into a volume-reduced form having a generally coiled, tubular configuration for insertion within a microcatheter, the edges of the distal portion being overlapped in the volume-reduced coiled configuration such that in the volume-reduced coiled configuration the self-expanding member has multiple layers in at least one radial direction. The self-expanding member can have a radial force measurement greater than or equal to 0.0010 N/mm and a chronic outward force of less than or equal to 0.026 N/mm as measured using a thin film method of testing, and a radial force measurement of between approximately 6 to 37 gf/in as measured using a two-pin method of testing.

DETAILED DESCRIPTION OF THE DRAWINGS

These and other features and advantages of the present embodiments will become more apparent upon reading the following detailed description and with reference to the accompanying drawings of the embodiments, in which.

Figure 1:
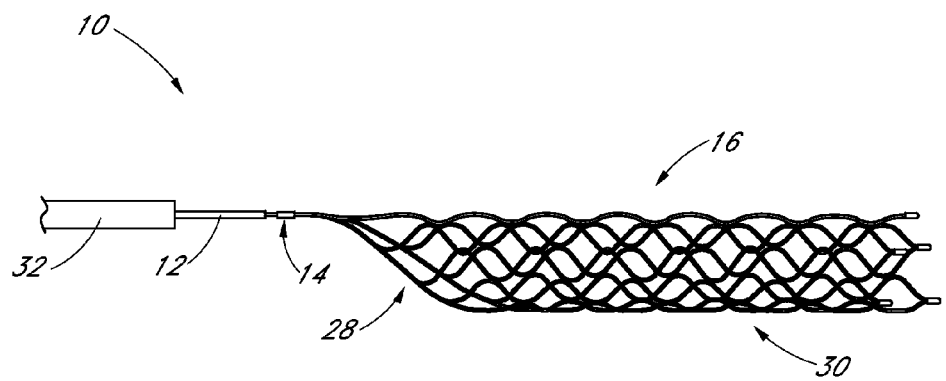
FIG. 1 is a side elevational view of a device for blood flow restoration and/or for use as an implantable member according to one embodiment, including a self-expanding member.
Figure 2:
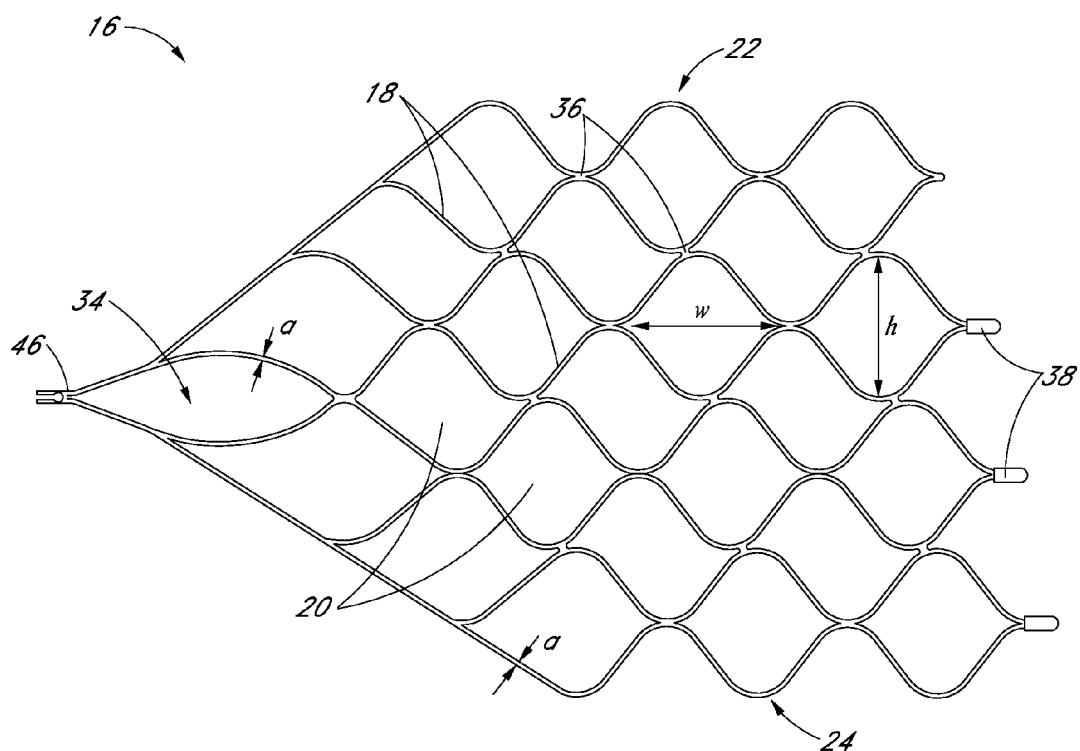
FIG. 2 is an illustration of the self-expanding member of the device of FIG. 1 in an unrolled, open state.
Figure 6A:
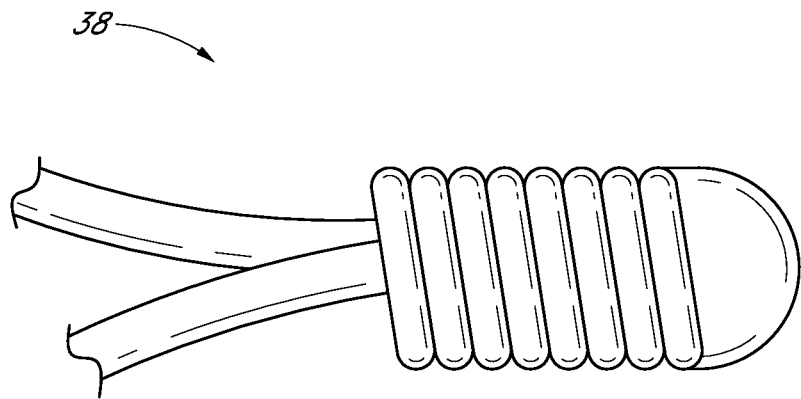
FIG. 6A is a side elevational view of a distal element of the self-expanding member of FIG. 2.
Figure 6B:
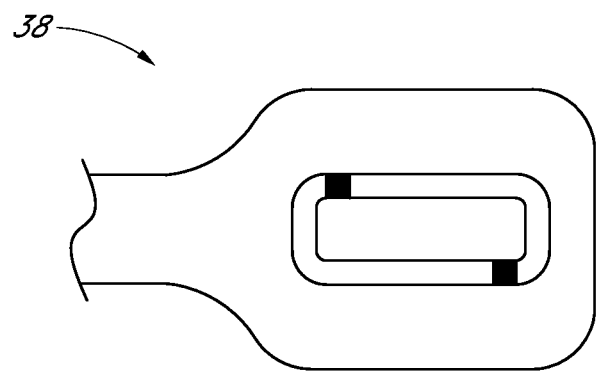
Figure 6C:
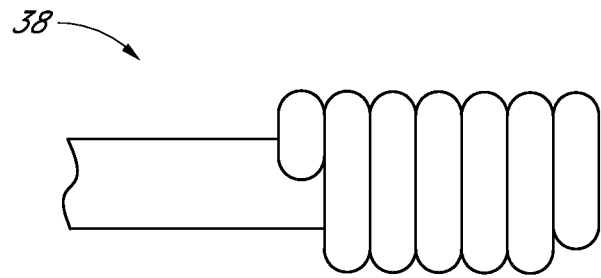
Figure 6D:
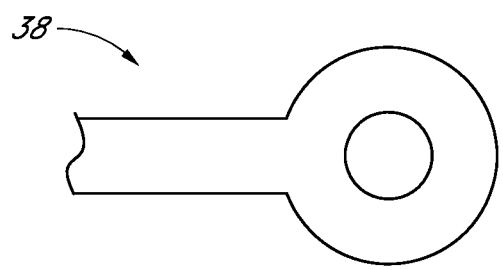
Figure 6E:
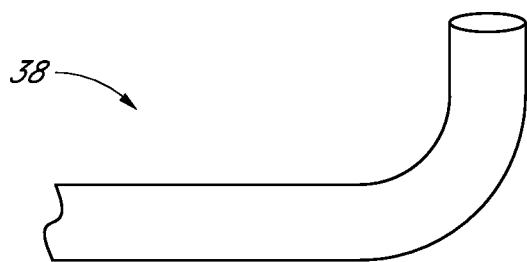
Figure 7:
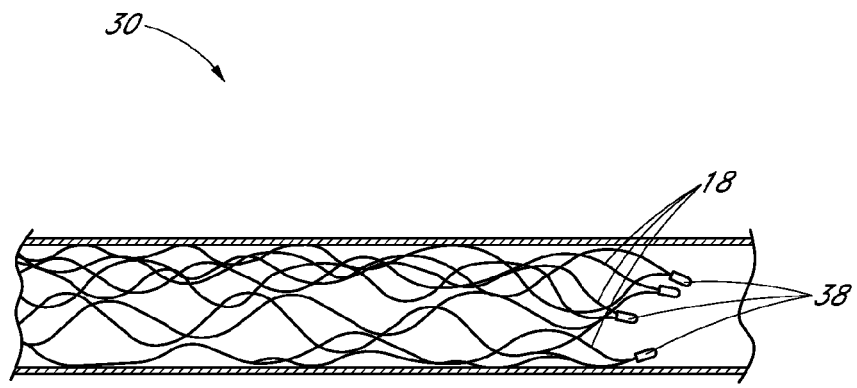
Figure 8A:
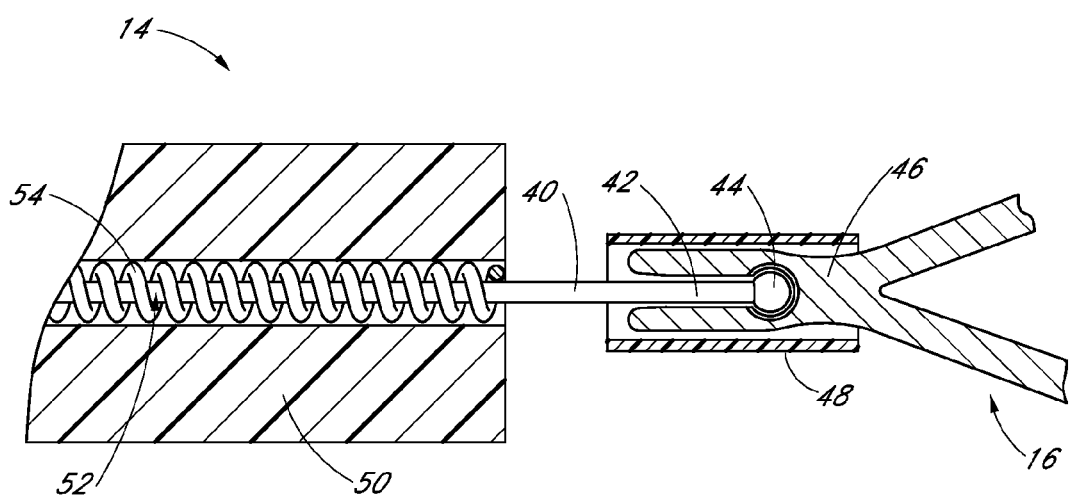
Figure 9A:
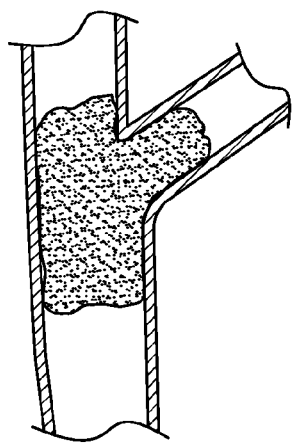
Figure 9B:
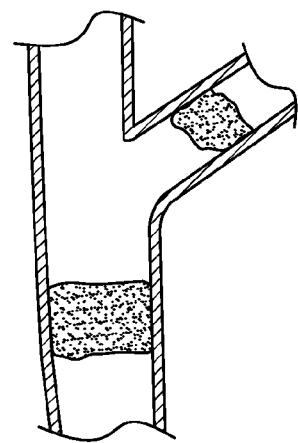
Figure 9C:
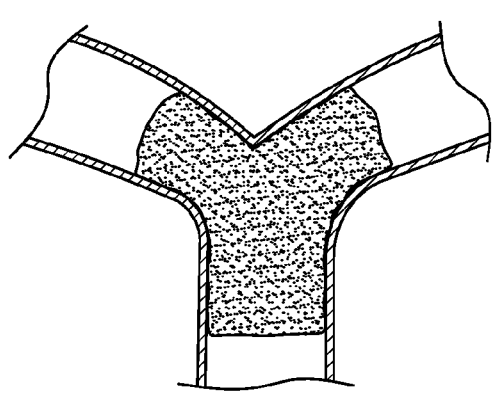
Figure 9D:
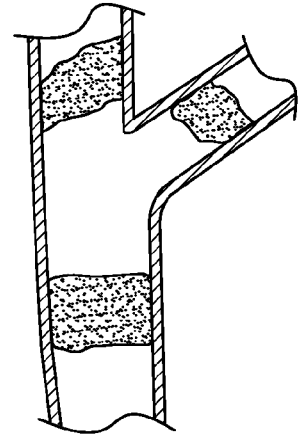
Figure 9E:
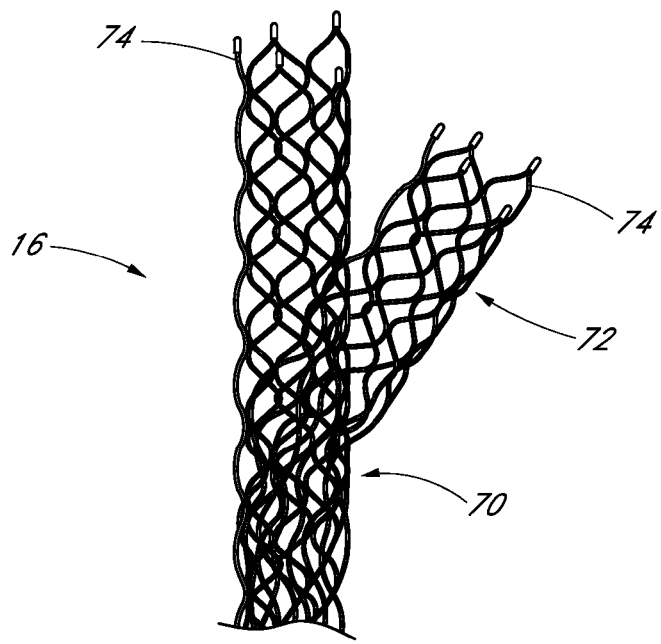
Figure 9F:
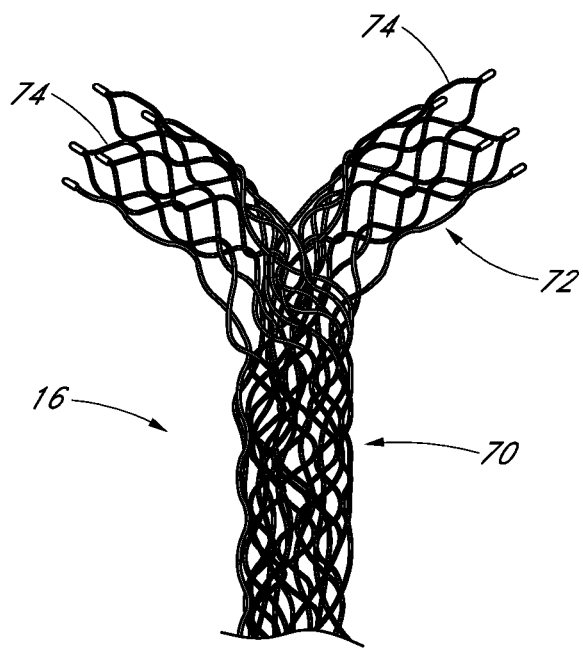
Figure 10:
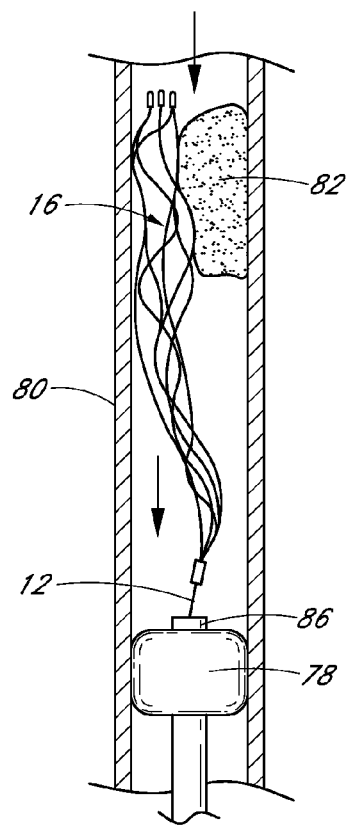
Figure 10:
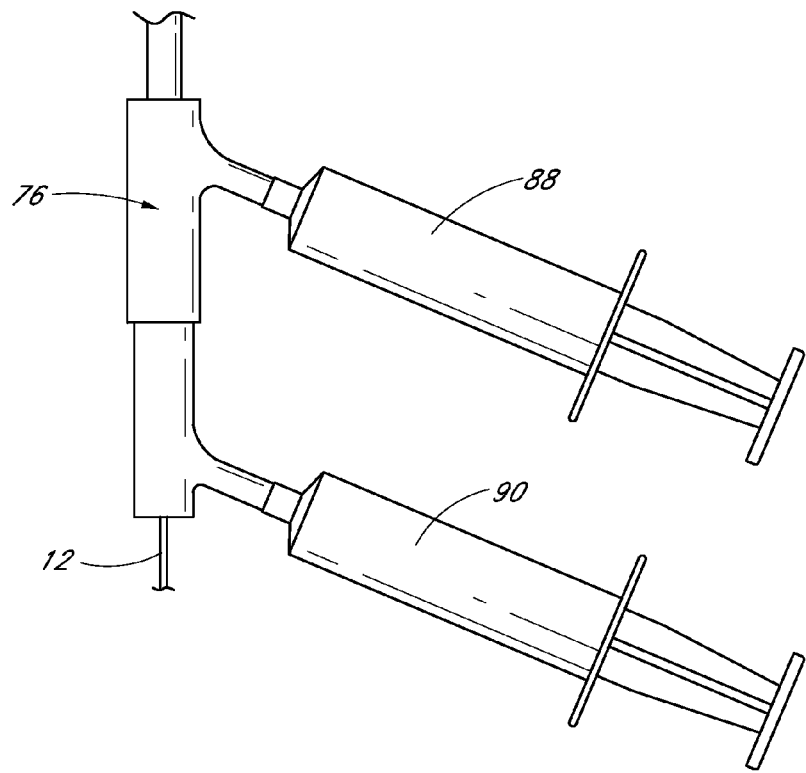
Figure 11:
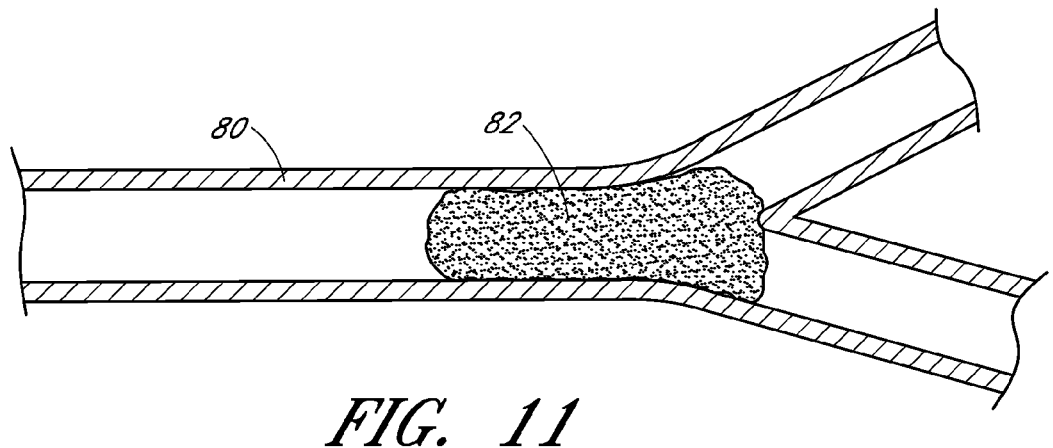
Figure 12:
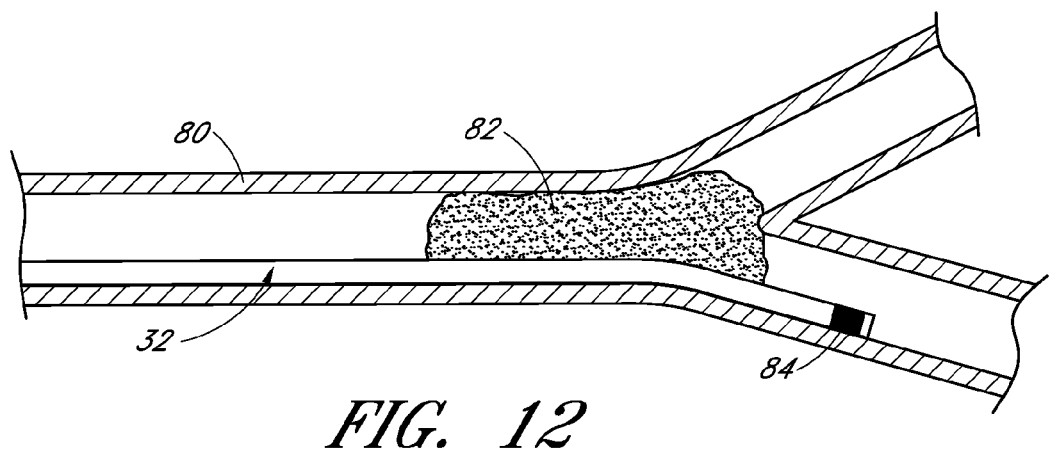
Figure 16A:
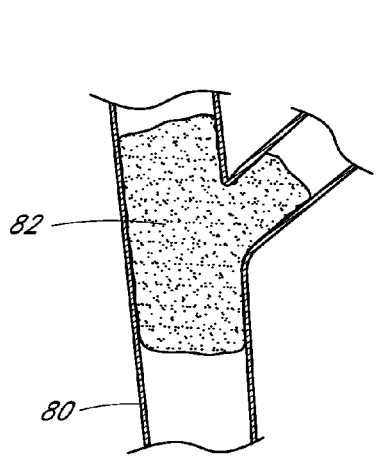
Figure 16B:
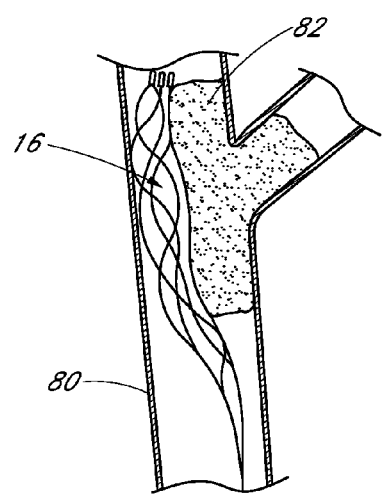
Figure 16C:
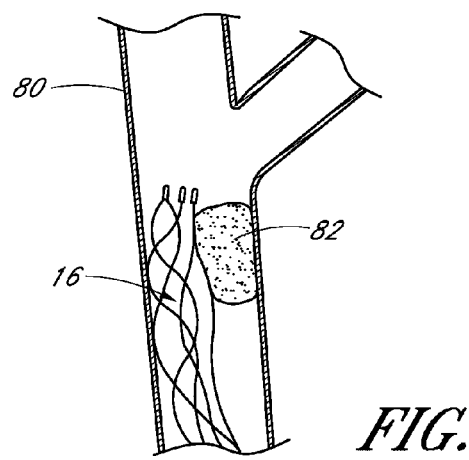
Figure 17:
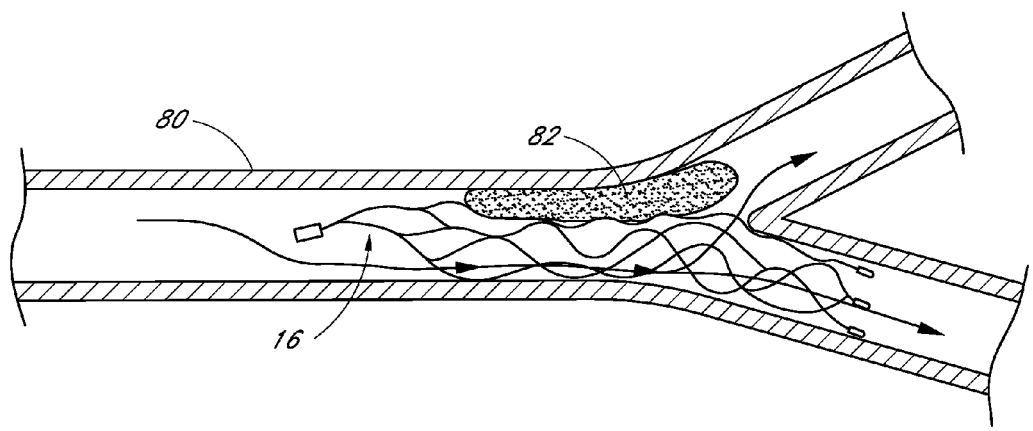

FIGS. 6B-E are side elevational views of alternative embodiments of the distal element of FIG. 6A;

FIG. 7 is a side elevational view of an embodiment of an inward bend for the self-expanding member of FIG. 2 to aid in thrombus removal;

FIG. 8A is a side elevational view of the detachment mechanism of the device of FIG. 1;

FIGS. 8B and 8C are side elevational views of alternative embodiments of the detachment mechanism of FIG. 8A;

FIGS. 9A-9D are schematic illustrations of thrombi located in bifurcations, bi-vessels, and/or multi-vessels;

FIGS. 9E and 9F schematic illustrations of embodiments of a device for blood flow restoration and/or for use as an implantable member, designed specifically for bifurcations, bi-vessels, and/or multi-vessels;

FIG. 10 is a schematic illustration of a system for use in blood flow restoration that includes the device of FIG. 1;

FIGS. 11-15 are schematic illustrations of method steps for restoring blood flow in a body using the system of FIG. 10;

FIGS. 16A-C are schematic illustrations of a method of restoring blood flow at a bifurcation; and FIG. 17 is a schematic illustration of the device of FIG. 1, with the self-expanding member in a detached state.

DETAILED DESCRIPTION OF THE PREFERRED EMBODIMENTS

Unless defined otherwise, all technical and scientific terms used herein have the same meanings as commonly understood by one of ordinary skill in the art. Although any methods and materials similar or equivalent to those described herein can be used in the practice or testing of the embodiments described herein, the preferred methods, devices, and materials are described herein.

Devices

With reference to FIGS. 1-3, a device 10 for flow restoration and/or for use as an implantable member can comprise a guidewire 12, a connection mechanism 14, and a self-expanding member 16.

The self-expanding member 16 can comprise a mesh structure. The mesh structure can be formed, for example, by laser cutting a preformed tube (i.e. by etching), by interconnecting a multitude of filaments by laser welding, or by other suitable methods. In a preferred arrangement, the self-expanding member 16 is initially laser cut from a tube, such that a longitudinal slit (i.e. cut) along a length of the device is present, for example as seen in FIGS. 1-3. In alternative embodiments, the self-expanding member can be formed by cutting a mesh pattern on a flat sheet and then rolling the flat sheet into a generally tube-like or coiled shape. Other methods for forming the self-expanding member 16 are also possible.

In a preferred arrangement, the self-expanding member 16 can be formed from alloys having shape-memory properties, such as NITINOL®, though other materials are also possible. In some embodiments the self-expanding member 16 can be subjected to a tempering treatment at temperatures customarily applied to the material so that the impressed structure is permanently established.

Figure 3A:
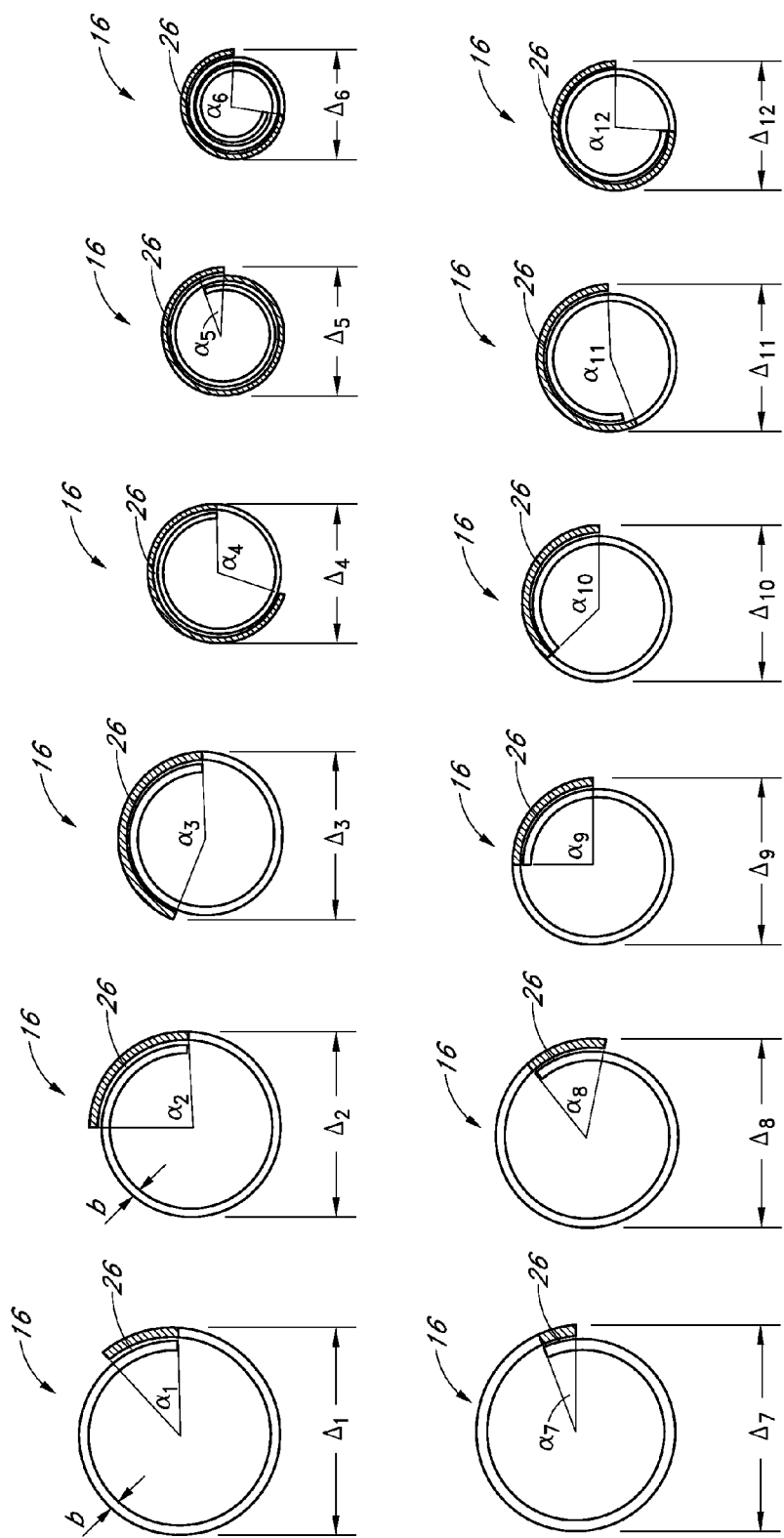
FIG. 3A is a schematic illustration of overlap configurations of the self-expanding member of FIG. 2, as seen from a distal end.
Figure 3B:
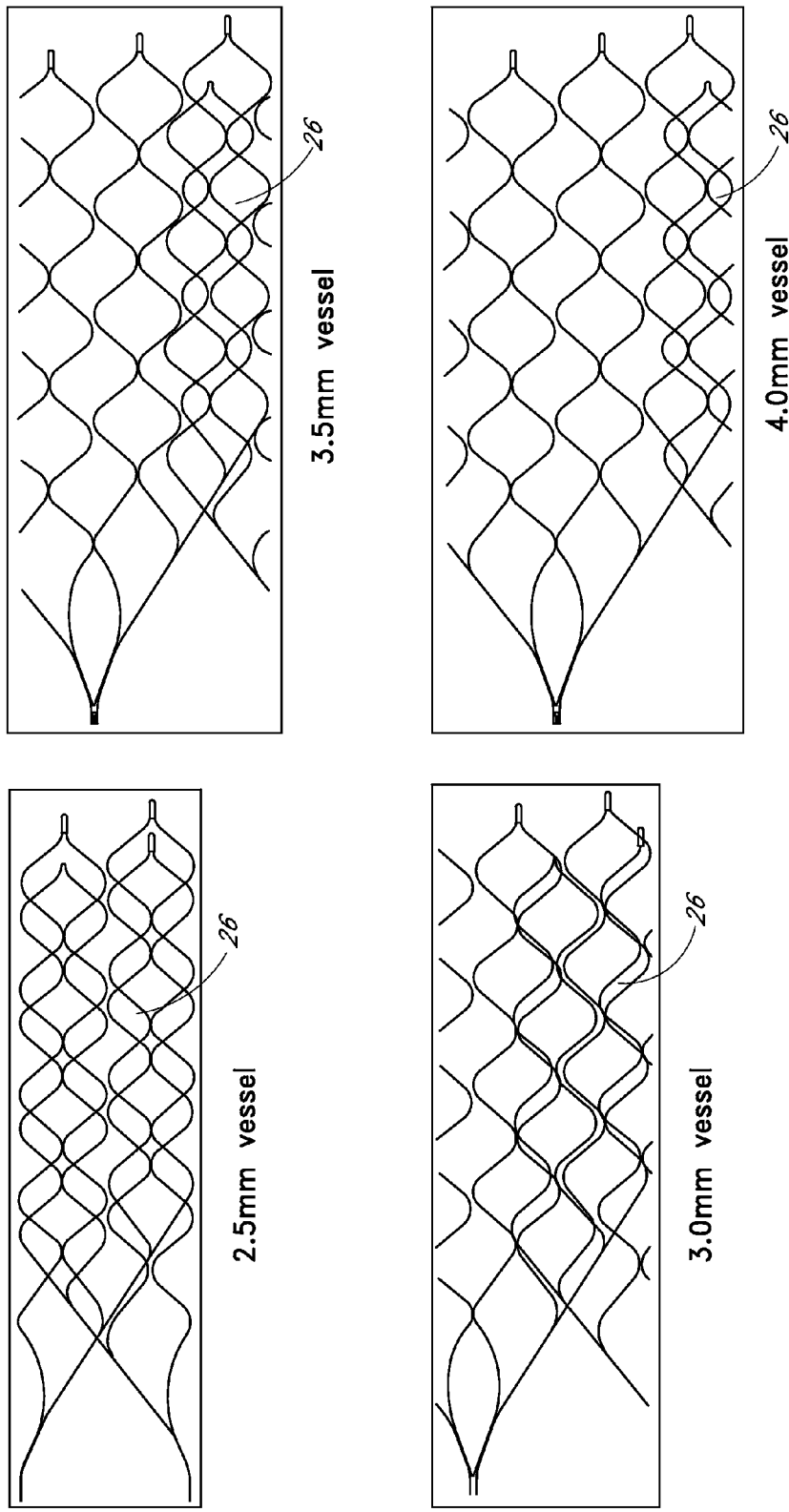
FIG. 3B is a schematic illustration of overlap configurations of the self-expanding member of FIG. 2, as seen from a side elevational view.

With continued reference to FIGS. 2, 3A, and 3B, the self-expanding member 16 can comprise a plurality of individual filaments 18 and individual cells 20, as well as a first edge 22 and a second edge 24. The first edge 22 and second edge 24 can be formed, for example, from cutting a preformed, etched tube longitudinally along the length of the tube. While the first edge 22 and second edge 24 are shown as having an undulating, or sinusoidal pattern, in some embodiments the first and second edges 22, 24 can have a straight, or linear configuration, or any other suitable configuration. Similarly, while the individual filaments 18 are shown having a particular undulating or sinusoidal pattern, in other embodiments the individual filaments 18 can have different patterns.

With continued reference to FIGS. 2, 3A, and 3B, the self-expanding member 16 can be curled such that edges 22 and 24 overlap one another when the self-expanding member 16 is in a volume-reduced form. While in a volume-reduced form, the self-expanding member 16, similar to a wire mesh roll, or piece of paper, can be curled up such that it can be introduced into a microcatheter and moved within the microcatheter. The self-expanding member 16 can have a central longitudinal axis while in both a volume-reduce form and when fully or partially expanded. Upon release from the microcatheter, the curled-up self-expanding member 16 can spring open and attempt to assume a fully expanded shape. Upon expansion, the self-expanding member 16 can expand towards an inner wall of a vessel, or towards a thrombus occluding the inner wall of a vessel. The extent of any overlap of the self-expanding member 16 within the vessel after expansion can be governed by the vessel size. For example, in narrower vessels a greater overlap of the edges 22 and 24 can occur, whereas in wider vessels the overlap can be smaller, or even an "underlap" may occur, in which case the edges 22 and 24 are separated by an open gap or space within the vessel.

The self-expanding member 16 can have various lengths and diameters. In some embodiments, the self-expanding member 16 can have lengths, measured proximally to distally along the longitudinal axis, ranging from 15 mm to 40 mm, though other ranges and sizes are also possible. The self-expanding member 16 can also have specific diameters, the diameters being measured when the self-expanding member 16 is fully free to expand. In some embodiments, the self-expanding member 16 can have a diameter of between approximately 3 mm and 4 mm so as to be used in size 18 microcatheters (i.e. microcatheters with an inner diameter of approximately 0.21 inch). In some embodiments the self-expanding member 16 can have a diameter of between approximately 5 mm and 6 mm so as to be used in size 27 microcatheters (i.e. microcatheters with an inner diameter of approximately 0.027 inch). Other ranges and values are also possible.

With continued reference to FIGS. 3A and 3B, embodiments of the self-expanding member 16 can experience various degrees of overlap in a volume-reduced form, forming zones of overlap 26. The self-expanding member 16 can assume various diameters $\Delta_1$, $\Delta_2$, etc., depending on the degree of the overlap (e.g. represented by angle $\alpha_1$, $\alpha_2$, etc.). As illustrated in FIG. 3B, the overlap zones 26 can vary in size and configuration depending on the vessel size. When inside a vessel, the overlap zone 26 of the self-expanding member 16 can advantageously provide grip and/or retaining ability with respect to a thrombus. For example, when the self-expanding member 16 expands against a thrombus, the individual filaments 18 and individual cells 20 of the overlap zone 26 can embed into and grip, or retain, the thrombus. The overlap zone 26 can provide added grip or retention due to the fact that there are multiple layers of filaments 18, in a radial direction, that act to grip or retain the thrombus. Thus, instead of just one layer of filaments 18 embedding into the thrombus, the overlap zone 26 can comprise two or more layers of filaments 20 that embed into the thrombus. The overlap zone 26 can prove particularly useful when attempting to remove a thrombus, since the layers of filaments 18 can inhibit the thrombus from slipping and/or sliding away from the self-expanding member 16.

Additionally, where the self-expanding member 16 has a longitudinal slit, or other type of slit (e.g. a slit at an angle relative to a longitudinal axis of the self-expanding member 16), the individual cells 20 can advantageously retain their general shape upon expansion. For example, while the self-expanding device 16 is expanding within a vessel, the cells 20 can generally retain the shape illustrated in FIG. 2 due to the fact that the first and second edges 22, 24 are free to move relative to one another. Without a slit, or open tube design, the shape of the individual cells 20 could tend to distort, (e.g. narrow or widen), as the self-expanding device 16 expands and contracts. This change in shape of the individual cells 20 can disadvantageously cause the self-expanding device 16 to lose its grip on the thrombus. This change in shape can also disadvantageously cause the individual cells 20 to "pinch" off portions of the thrombus as the cells 20 change shape, thus allowing thrombus debris (e.g. small pieces of the thrombus) to escape and raise the likelihood of clots developing further downstream.

In some embodiments, the self-expanding member 16 can comprise a proximal portion 28 and a distal portion 30. As illustrated in FIGS. 1 and 2, the proximal portion 28 can comprise a taper. In some embodiments, the proximal portion 28 can have individual cells 20 that have a different size than the individual cells 20 of the distal portion 28. For example, in some embodiments, the proximal portion 28 can have individual cells 20 that have a size larger than that of the individual cells 20 of the distal portion 30. The proximal portion 28 can taper gradually towards the connection mechanism 14, or some other connection point along the device 10 that connects the self-expanding member 16 to the guidewire 12. For example, in some embodiments the connection mechanism 14 can comprise a generally non-detachable interface or transition point between the self-expanding member 16 and the guidewire 12. In some embodiments the connection mechanism 14 can be integrally formed with the guidewire 12 and self-expanding member 16.

The taper of proximal portion 28 can be at various angles relative to the guidewire 12. For example, in some embodiments, the taper can have an angle of approximately 45 degrees relative to the guidewire 12, though other angles are also possible. In some embodiments, the taper can form a generally "s"-shaped structure along the edges 22, 24 such that the edges 22, 24 do not extend straight from the distal portion 30 to the connection mechanism 14. In some embodiments the "s"-shape can give the taper portion 28 a more smooth transition between the proximal portion 28 and distal portion 30, and reduce stresses within the individual filaments 18.

In some embodiments, the taper of proximal portion 28 can advantageously facilitate retraction and repositioning of the device 10 and self-expanding member 16.

In some embodiments, the tapered proximal portion 28 can also be designed to generally not contact the vessel wall during a blood flow restoration procedure, and to generally not interfere with the flow of blood within a vessel. For example, in some embodiments generally only the distal portion 30, and its individual filaments 18 and individual cells 20, contact a vessel wall and/or thrombus.

With continued reference to FIGS. 1-3, the self-expanding device 16 can be designed to engage and remove thrombi that are both generally soft, or malleable, or generally hard, or callous. As described above, many current devices are designed to pierce through a thrombus, and then remove the thrombus by pulling proximally, or are designed to deploy completely distal of the thrombus before engaging and removing the thrombus. These devices do not work well for engaging and removing both soft and hard thrombi of varying thickness and location.

The self-expanding member 16 described above, however, can advantageously be designed to engage both soft and hard thrombi of varying thickness and location. For example, the self-expanding member 16 can be designed to have specific filament lengths, widths, and, thicknesses, such that the self-expanding member 16 is optimally configured to engage and remove a wide range of thrombi.

With reference to FIGS. 2 and 3A, in a preferred arrangement the individual filaments 18 in the proximal portion 28 can have individual filament widths "a" that range from 0.040 mm to 0.090 mm, and individual filament thicknesses "b" that range from 0.045 mm to 0.080 mm, though other ranges and values for individual filament width and thickness in the proximal portion 28 are also possible. Widths "a" as described herein can generally measured as illustrated by the arrows in FIG. 2. Thicknesses "b", as described herein for filament width, can generally be measured as illustrated by the arrows in FIG. 3 (e.g. in a direction extending out of the page of FIG. 2, and perpendicular to the measurement for width "a"). The widths "a" can be measured, for example, using a system such as the Visicon Automated Inspection System, or other suitable system. The thicknesses "b" can be measured, for example, using a system such as the Heidenhain Inspection System, or other suitable system.

With continued reference to FIG. 2, in a preferred arrangement the self-expanding member 16 can include a "teardrop" region 34 in the proximal portion 28. The teardrop region 34 can comprise one of the individual cells 20 described above, and can include individual filaments 18 that are wider, and/or stronger, than other filaments 18 in the self-expanding member 16. The teardrop region 34 can provide added stability and strength to the self-expanding member 16 in the tapering portion to facilitate retrievability of the self-expanding member 16 into the microcatheter 32, and/or to facilitate repositioning of the self-expanding member 16. For example, the teardrop region 34 can have filaments 18 with individual filament widths "a" that range from 0.080 mm to 0.14 mm, though other ranges and values are also possible. With continued reference to FIG. 2, the self-expanding member 16 can further include a connector filament 36. The connectors filaments 36, in a preferred arrangement, can have an individual filament thickness "b" that ranges from 0.050 mm to 0.0825 mm and an individual filament width "a" that ranges from 0.050 mm to 0.0825 mm, though other ranges and values are also possible. With continued reference to FIG. 2, in a preferred arrangement the individual filaments 18 in the distal portion 30 of the self-expanding member 16 can have individual filament thicknesses "b" that range from 0.040 mm to 0.075 mm, and individual filament widths "a" that range from 0.038 mm to 0.082 mm, though other ranges and values are also possible. In some embodiments the individual filaments in the distal portion 30 of the self-expanding member 16 can have average filament thicknesses "b" that range from 0.048 mm to 0.067 mm, and individual filament widths "a" that average from 0.053 mm to 0.067 mm, though other ranges for average values are also possible.

With continued reference to FIG. 2, the individual cells 20 of the self-expanding member 16 can also be designed and sized such that the self-expanding member 16 is optimally configured to engage and remove a wide range of thrombi. For example, in a preferred arrangement the individual cells 20 in the distal portion 30 of self-expanding member 16 can have a width, as measured along a longitudinal axis of the self-expanding member 16 (labeled "w" in FIG. 2), of between 3.50 mm to 5.50 mm, though other ranges and values are also possible. The individual cells 20 in the distal portion 30 can further have a height, as measured along a direction perpendicular to the width (labeled "h" in FIG. 2), of between 2.50 mm to 4.50 mm, though other ranges and values are also possible. In some embodiments, the cell sizes in the proximal portion 28 and/or distal portion 30 can vary, as can the individual filament thicknesses and widths within the proximal and/or distal portions 28, 30. In a preferred arrangement, a self-expanding member 16 with a generally large cell size (e.g. a cell size of 3.5 mm by 2.50 mm) can provide for high circumferential conformity, flexibility, and axial rigidity, thereby promoting capture and removal of a wide range of thrombi.

With continued reference to FIG. 2, it has been found that the relationship between the total filament length of the self-expanding member 16 and the total length of the thrombus to be removed can help determine whether the self-expanding member 16 is optimally configured to engage and remove a particular sized thrombus.

For example, the total filament length can be found by measuring the total available filament length exposed to the thrombus length using a program such as SolidWorks. The total available filament length is equivalent to the combined total lengths (length being measured by following along the path of each filament for example in FIG. 2) of all the filaments in the distal portion 30 of self-expanding member 16 or that portion of the self-expanding member 16 that is generally exposed to the thrombus. The total thrombus length can be found, for example, by crossing a thrombus with a microcatheter and injecting contrast agent through the microcatheter distally of the thrombus, and then injecting contrast agent through a guide catheter proximally of the thrombus, so as to visualize and measure the length of the thrombus. In a preferred arrangement, the ratio of the total filament length to the total thrombus length is between 10 to 15, though other ranges and values are also possible. Therefore, a self-expanding member 16 that has for example a total filament length of 255 mm, and a filament length to thrombus length ratio of 12.75, is ideally suited to engage and remove thrombi that range up to 20 mm in length.

Figure 4:
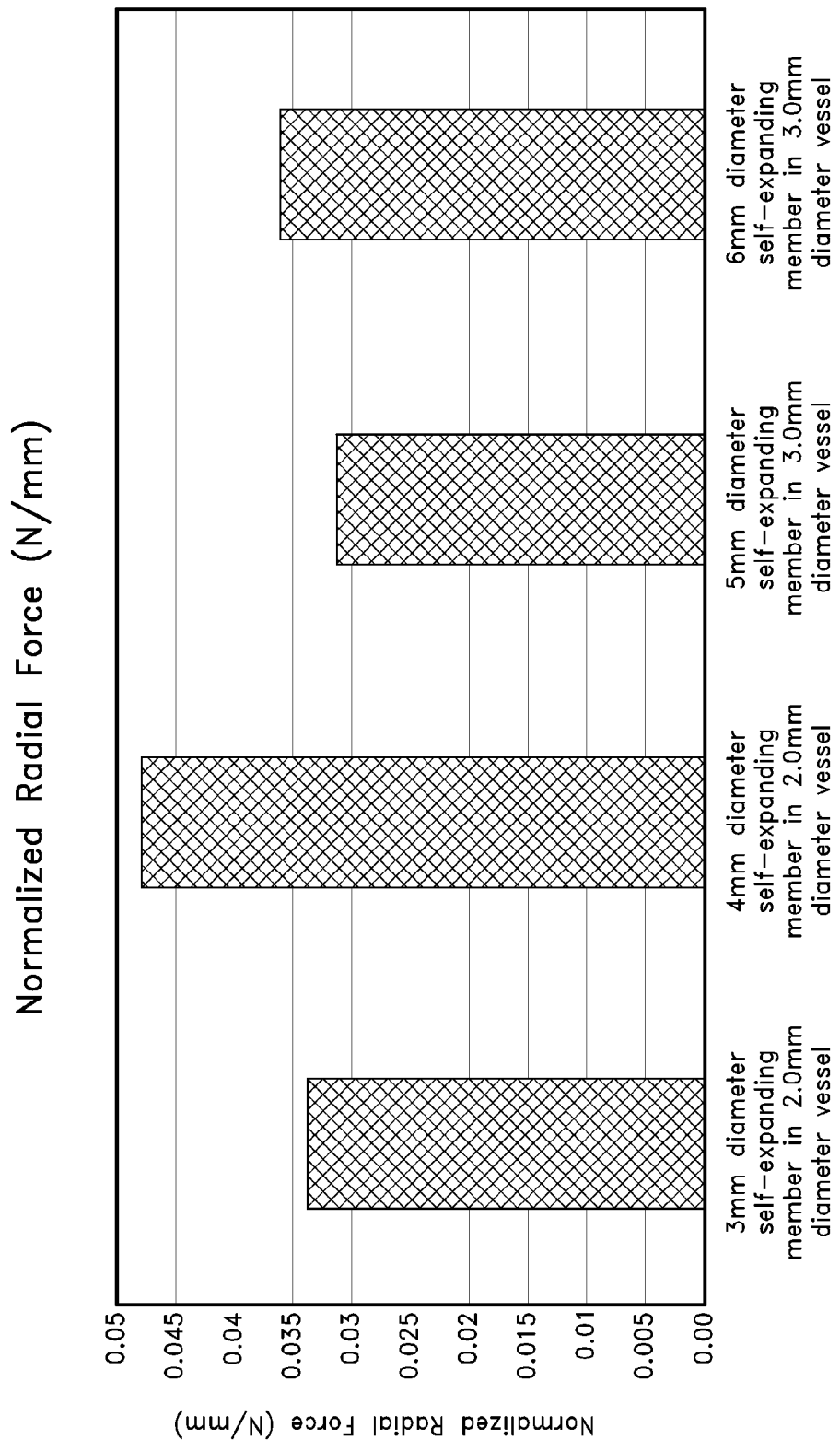
FIG. 4 is a chart illustrating data collected on normal radial forces exerted by various embodiments of the self-expanding member of FIG. 2.
Figure 5:
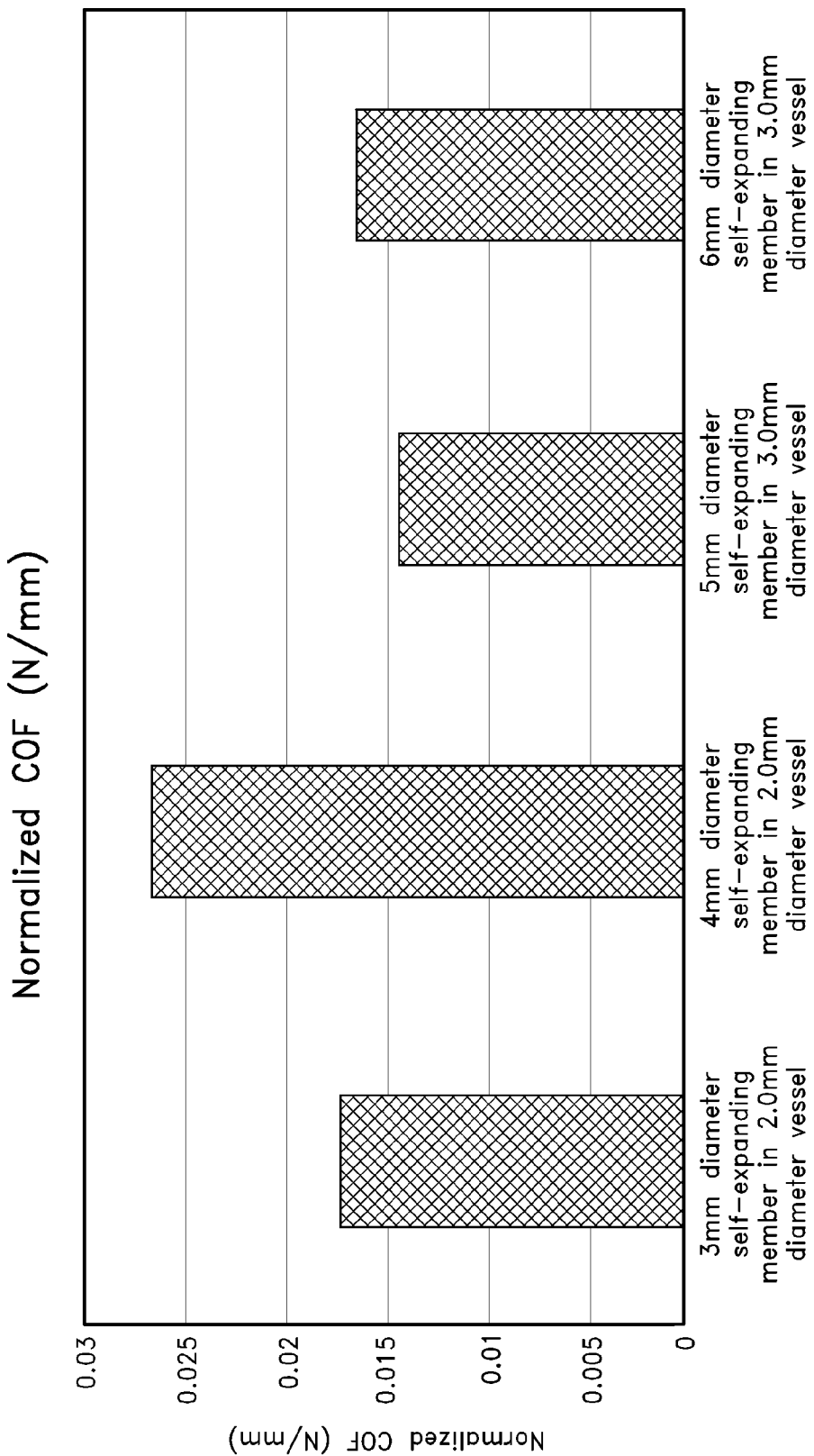
FIG. 5 is a chart illustrating data collected on chronic outward forces exerted by various embodiments of the self-expanding member of FIG. 2.

With reference to FIGS. 4 and 5, the self-expanding member 16 can further be designed to generate specific forces once it is deployed and released from the microcatheter 32 in order to optimally engage and remove a wide range of both soft and hard thrombi. By deploying the self-expanding member 16 across a thrombus, the self-expanding member 16 can self-expand to a larger diameter due to elastic energy stored in the self-expanding member 16. The self-expanding member 16 can expand in the vessel until equilibrium is reached between the stored elastic energy and an opposing force from the surrounding vessel wall and/or thrombus. The filaments 18 and cells 20 of the self-expanding member 16 can penetrate a thrombus, promoting adhesion and embedment of the thrombus to the self-expanding member 16, and the expanding force of the self-expanding member 16 can promote dislodgment of the thrombus from the vessel wall.

For example, the stored elastic energy of the self-expanding member 16 can generate outward forces known as radial force (RF) and chronic outward force (COF). The radial force is equivalent to the outward force exerted by the self-expanding member 16 during compression of the self-expanding member 16. The chronic outward force is equivalent to the outward force exerted by the self-expanding member 16 during decompression, or expansion, of the self-expanding member 16. In a preferred arrangement, the COF can be designed so that it is not so high that it bursts, or damages, a vessel wall. In a preferred arrangement, the RF can be designed so that it is high enough to resist compression forces from the surrounding vessel environment, maintain patency of the vessel lumen, and restore flow through the thrombus site.

During deployment and thrombus retrieval, the highest COF and RF can occur when the self-expanding member 16 is deployed and/or retrieved inside a minimum recommended diameter vessel. Conversely, the COF and RF can be the lowest when the self-expanding member 16 is deployed and/or retrieved inside a maximum recommended diameter vessel. The curled, overlap nature of the self-expanding member 16 can enhance the COF and RF, particularly in smaller diameter vessels, to allow for increased embedment of a thrombus to the self-expanding member 16.

By considering such factors including but not limited to anatomy, physiological environment, blood vessel mechanical properties, flow properties, pressures, stresses, and strains, methods have been developed to determine optimal radial and chronic outward forces for the self-expanding member 16.

The radial force can be measured by various methods. For example, a two pin method can measure the radial force by placing (e.g. sliding) the self-expanding member 16 over two elongate, parallel pins, such that the generally tubular, self-expanding member 16 encompasses and surrounds the two pins. When placed over the two pins, the proximal taper on proximal portion 28, and the keyway structure 46, can be located generally halfway between the two elongate pins, and to one side. The ends of the two pins can be placed in a tensile testing machine. When the testing machine is loaded, the machine can cause the pins to pull apart from one another, such that a force is imparted on the self-expanding member 16. When the self-expanding member 16 slips off of one of the pins, the radial force can be measured.

A thin film method can also be used to measure the radial force, and can additionally be used to measure the chronic outward force. The thin film method can generally comprise compressing and decompressing the self-expanding member 16 circumferentially 360 degrees using a thin film of PTFE wrapped around the self-expanding member 16. The thin film method can measure changes in diameter of the self-expanding member 16 versus force for both expansion and contraction of the self-expanding member 16.

In a preferred arrangement using the thin film method, the self-expanding member 16 can have a radial force measurement greater than or equal to 0.0010 N per mm of length of the portion of the self-expanding member 16 that is configured to contact a vessel wall or thrombus (e.g. distal portion 30). The length in this unit refers to a proximal to distal direction measurement (i.e. moving left to right in FIG. 1). The self-expanding member 16 can have a chronic outward force of less than or equal to 0.026 N per mm of length of the portion of the self-expanding member 16 that is configured to contact a vessel wall or thrombus. In a preferred arrangement using the two pin method, the self-expanding member 16 can have a radial force measurement of between approximately 6 to 37 gf per inch of length of the portion of the self-expanding member 16 that is configured to contact a vessel wall or thrombus.

FIGS. 4 and 5 illustrate test measurements that were taken on a variety of differently sized self-expanding members 16, in a variety of differently sized vessel diameters, showing how the radial and chronic outward forces can vary depending on the size of the self-expanding member 16 and the size of the vessel. In the charts, a 3 mm diameter, 4 mm diameter, etc. self-expanding member refers generally to the diameter of the self-expanding member 16 when unconstrained.

By considering such factors including but not limited to anatomy, physiological environment, blood vessel mechanical properties, flow properties, pressures, stresses, and strains, methods have also been developed to determine optimal dislodgment forces for the self-expanding member 16. The dislodgment force is the force required to cause a fully deployed self-expanding member 16 to slip axially along a vessel (e.g. artery) wall. Determining a lower bound dislodgment force can help ensure that the self-expanding member 16 can withstand its physiological environment (e.g. forces due to blood flow and shear stress) without dislodgment from its deployed location. Determining an upper bound dislodgment force can help to evaluate the ability of the vessel to withstand retrieval of the self-expanding member 16 and device 10 without causing unintended dissection or damage to the vessel wall. A dislodgment testing method, for example, can include measuring the force required to cause a fully deployed self-expanding member 16 to slip axially along an in vitro model simulating an artery by pulling the device along a specified length in the tubing and recording the force at which slippage occurs. The dislodgment test comprises pulling the self-expanding member 16 once along a specified length through a section of tubing and recording the force at which slippage occurs. In a preferred arrangement, the self-expanding member 16 can have a dislodgment force that ranges between 0.010 N and 0.700 N, though other ranges and values are also possible.

With reference to FIGS. 2, 6, and 7, in some embodiments the self-expanding member 16 can further include at least one distal element 38. The distal element 38 can be attached to or integrally formed with the distal portion 30. The distal element 38 can comprise, for example, a platinum distal marker band. As a marker band, the distal element 38 can be used during an imaging process to identify a location or locations of the self-expanding member 16 during a blood flow restoration procedure. PCT Publication No. WO 2009/105710, which is incorporated by reference in its entirety, describes various uses of marker bands and imaging of a self-expanding member 16.

In a preferred arrangement, the self-expanding member 16 can comprise a plurality of distal elements 38. For example, in some embodiments the self-expanding member 16 can comprise three or four distal elements 38, arranged generally circumferentially along the distal end of the self-expanding member 16, though other numbers and/or arrangements are also possible. The distal elements 38 can comprise "hook-like" elements for ensnaring, capturing, and/or gripping portions of a thrombus. For example, it has been found that using the configuration of the distal element 38 illustrated in FIG. 6A can be useful in retrieving thrombi. In particular, it has been found that in embodiments where there are three or four such distal elements 38 along the end of the self-expanding element 16, the distal elements 38 themselves are alone able to capture a thrombus and/or help with thrombus retention during retrieval of the thrombus. Because the distal elements can protrude inward slightly from the rest of the self-expanding member 16, the thrombus can adhere to the shape of the distal elements 38. In some embodiment the distal elements 38 can be staggered both circumferentially and longitudinally along the distal end of the self-expanding member 16. The staggered placement of distal elements 38 can allow the thrombus to adhere to multiple distal elements 38, for example at different locations along the length of the thrombus.

Additionally, in some embodiments, the distal end of the self-expanding member 16 can include filaments 18, and/or distal elements 38, that are angled relative to the rest of the distal portion 30 of self-expanding member 16. For example, and with reference to FIG. 7, in a preferred arrangement, the distal end of self-expanding member 16 includes filaments 18 that are bent inwardly (i.e. towards a central longitudinal axis of the vessel lumen). The bent or angled filaments 18, which can include the distal elements 38, can contribute to and facilitate capture of and retention of the thrombus during retrieval. For example, if the thrombus begins to move distally along the self-expanding member 16 (i.e. if the thrombus begins to "slip" away) during retrieval, the thrombus can become caught in the slight inward bend of the filaments 18 and/or distal elements 38. While the embodiments shown include bends that angle inwardly, in other embodiments the bends can angle outwardly (i.e. away from the central axis of the lumen). Additionally, the degree of the angle relative to the central longitudinal axis of the vessel can vary. In some embodiments, for example, the filaments 18 along the distal end of the self-expanding member 16 can be angled between approximately 10 to 30 degrees relative to the central longitudinal axis. In some embodiments the filaments 18 can be angled at approximately 20 degrees. In some embodiments the filaments 18 can be angled at approximately 30 degrees. Other angles, and ranges for angles, are also possible.

With reference to FIGS. 1, 8A, and 8B, in some embodiments the connection mechanism 14 can comprise a releasable connection mechanism for easily releasing the self-expanding mechanism 16. In some embodiments, the connection mechanism 14 can form a connection point between the guidewire 12 and self-expanding member 16, and not be intended to release the self-expanding member 16. In some embodiments, the connection mechanism 14 can form part of the guidewire 12 and/or self-expanding member 16.

Depending on the procedure and intended use of the self-expanding member 16, it can be advantageous to have a connection mechanism 14 that permits release of the self-expanding member 16. For example, during a blood flow restoration procedure, it can prove difficult and/or dangerous to fully retrieve a thrombus due to a complicated vasculature or the risk of damaging a vessel wall. Leaving the self-expanding member 16 behind may prove to be the only option available to a surgeon or other medical personnel. In other circumstances the self-expanding member 16 can include drug-eluting capabilities, and/or can be coated with a particular type of drug that facilitates thrombus dissolution. It can be advantageous in such circumstances to release the self-expanding member 16 and allow the self-expanding member to anchor the thrombus against the vessel wall while the thrombus is dissolved by the drug. Various types of materials, drugs, and/or coatings for a self-expanding member 16 are described, for example, in PCT Publication No. 32 WO 2009/105710, which is incorporated by reference in its entirety.

Additionally, while the self-expanding member 16 described above has been described in the context of use during a blood flow restoration procedure, the self-expanding member 16 can also, or alternatively, be used as an implantable member (e.g. stent). For example, the self-expanding member 16 can be released through the connection mechanism 14 at a stenosis, aneurysm, or other appropriate location in a vessel. The self-expanding member 16 can expand and engage a vessel wall so as to hold the vessel wall open and/or act as an occluding member. While the filament thicknesses, widths, cell sizes, and forces described above can be optimized for a self-expanding member 16 designed for flow restoration, these values can also be optimized for a self-expanding member 16 designed for use as an implantable member. In some embodiments they are the same values.

With continued reference to FIGS. 8A-8C, the connection mechanism 14 for releasing the self-expanding member 16 can comprise, for example, an electrolytically severable region 40. While other types of connection mechanisms are also possible (e.g. a purely mechanical connection or a connection that involves heating and melting a connection area), in a preferred arrangement the connection mechanism 14 comprises a connection that dissolves under the influence of electrical energy when in contact with an electrolyte. The electrolytically severable region 40 can comprise an exposed piece of electrolytically severable material, such as stainless steel, though other materials are also possible. The electrolytically severable region 40 can be coated with a strengthening material, such as parylene, though other types of coating material are also possible. In some embodiments, the electrolytically severable region 40 can comprise a portion of the guidewire 12. In a preferred arrangement, the length of the electrolytically severable region can range from 0.1 mm to 0.5 mm, and more preferable from 0.2 mm to 0.4 mm, though other ranges and values are also possible.

With continued reference to FIG. 8A, in a preferred arrangement the connection mechanism 14 can further comprise a stem 42 with a ball 44 located at a distal end of the stem 42. The stem 42 and/or ball 44 can be coated with insulative material and/or adhesive, to inhibit or prevent electric current from traveling through the connection mechanism 14 to the self-expanding member 16. The connection mechanism 14 can further comprise a keyway structure 46. The keyway structure 46 can comprise a slit and/or opening that is configured to receive the stem 42 and/or ball 44, and to lock the stem 42 and/or ball 44 in place. In some embodiments, the keyway structure 46 can comprise part of proximal portion 28 of the self-expanding member 16. In some embodiments the keyway structure 46 can comprise NITINOL®, though other materials are also possible.

With continued reference to FIG. 8A, in a preferred arrangement the connection mechanism 14 can further comprise a sleeve 48. The sleeve 48 can surround the keyway structure 46, stem 42, and/or ball 44. The sleeve 48 can be comprised of platinum, though other materials are also possible. The sleeve 48 can comprise, for example, a proximal radiopaque marker. The connection mechanism 14 can further comprise a shrink tubing 50 surrounding a distal guidewire section 52. In some embodiments the distal guidewire section 52 can comprise a coil 54. Similar to the severable region 38, the distal guidewire section 52 can be coated with parylene, though other materials are also possible.

Overall, the structure of connection mechanism 14 can be configured such that the self-expanding member 16 releases at a predetermined point. For example, the self-expanding member 16 can generally be isolated from electric current, such that during detachment of the self-expanding member 16, only the electrolytically severable region 40 disintegrates in blood, and the self-expanding member 16 separates from the guidewire 12 cleanly at the electrolytically severable region 40, and is released into the vessel.

With reference to FIGS. 8B and 8C, other embodiments and types of connection mechanisms 14 are also possible. For example, in both FIGS. 8B and 8C, the connection mechanism 14 can comprise a dumb-bell shaped element 56 that dissolves under the influence of electrical energy when in contact with an electrolyte. At the proximal (i.e. guidewire side) end of the dumb-bell shaped element 56, as per FIG. 8B, a spiral structure 58 can interact with a strengthening spiral 60 of the guide wire 12. At the distal end, a ball-shaped element 62 can be arranged that, with the help of a laser welding technique, is connected to a platinum spiral 64 which, in turn, is linked with a connection point 66 situated at a proximal end of the self-expanding member 16. In some embodiment the platinum spiral 64 can serve as an X-ray reflecting proximal marker of the self-expanding member 16. To strengthen the joint between the ball-shaped element 62 and the connection point 66, a reinforcement wire 68 can be provided. Alternatively, the platinum spiral 64 can also be designed to withstand tensile and thrust forces imposed upon it.

With continued reference to FIG. 8B, the dumb-bell shaped separating element 56 can include a steel material that is susceptible to corrosion in an electrolyte under the influence of electrical energy. To accelerate corrosion and shorten the separating time span, a structural or chemical weakening of the dumb-bell shaped element 56 can be beneficial, for example, by applying grinding methods or thermal treatment. In some embodiments, the portion of the dumb-bell shaped element 56 accessible to the electrolyte has a length of 0.1 mm to 0.5 mm, particularly 0.3 mm, though other ranges and values are also possible.

With continued reference to FIGS. 1 and 8B, the spiral structure 58 can be secured via welding both to the dumb-bell shaped element 56 and the reinforcement spiral 60 of the guide wire 12. The guide wire 12 itself can be slidably accommodated within the microcatheter 32.

With reference to FIG. 8C in some embodiments the dumb-bell shaped element 56 has a ball-shaped element 62 at each end. The ball shaped elements 62 can be connected distally to the connection point 66 of the self-expanding member 16 and proximally to the guide wire 12 via spirals 60, 64, respectively.

With reference to FIGS. 9A-F, in some embodiments the self-expanding member 16 can be designed specifically for use as a flow restoration device and/or an implantable member (e.g. stent) at a bifurcation, bi-vessel, and/or multi-vessel. For example, and with reference to FIG. 9A, thrombi can be located at bifurcations in the neurovasculature such as the internal carotid artery and the anterior cerebral artery, or internal carotid artery and middle cerebral artery, or the basilar artery and the posterior cerebral artery. With reference to FIG. 9B, thrombi can also be located at two vessels (i.e. bi-vessels) as two separate clots in similar vessels. With reference to FIGS. 9C and 9D, thrombi can also be located at multi-vessels as one clot that is within multiple vessels or as multiple clots that are within multiple vessels. Vessels with such clots can be located, for example, at the intracranial internal carotid, anterior cerebral and middle cerebral arteries, and basilar artery and both posterior and cerebral arteries.

With reference to FIGS. 9E and 9F, the self-expanding member 16 can have shapes and/or sizes that accommodate the types of vessel and clots illustrated in FIGS. 9A-D. For example, the self-expanding member 16 can have a proximal portion 70 similar to proximal portion 28 described above. The self-expanding member can further have a distal portion 72 that is divided into two or more branches 74. The branches 74 can be designed specifically, for example, for different types of bifurcations and splits commonly found in the neurovasculature. Similar to the distal portion 30 described above, the distal portion 72 can be configured to expand against a thrombus or vessel wall. At least a portion of the self-expanding member 16 can be slit and/or cut so as to facilitate the type of coiled configuration seen in FIGS. 3A and 3B. The self-expanding member 16 for use at bifurcations, bi-vessels, and/or multi-vessels can also similarly have the same types of filaments 18 and cells 20 as that of the self-expanding member 16 described above and illustrated in FIG. 2.

While embodiments of the device 10 have been described herein, various other embodiments of the device 10 can be found, for example, in U.S. Pat. No. 7,300,458, U.S. Patent Publication No 2008/0125855, and PCT Publication No. WO 2009/105710, each of which is incorporated by reference in its entirety.

Methods

With reference to FIGS. 10-15, and as described above, the device 10, including the guidewire 12 and self-expanding member 16, can be used as a flow restoration device. For example, the device 10 can be used to restore blood flow in a medical patient experiencing ischemic stroke due to large intracranial vessel occlusion. In a preferred arrangement, the device 10 can be used in conjunction with the microcatheter 32 and a balloon guide catheter 76 as seen for example in FIG. 10. The device 10 can retrieve thrombi from highly tortuous, small, and thin wall vessels. The device 10 can be used to treat vessels with diameters, for example, ranging from 2.0 mm to 5.5 mm, such as the internal carotid artery, M1 and M2 segments of the middle cerebral artery, anterior cerebral artery, basilar artery and vertebral artery, though other ranges, sizes, and particular vessels are also possible.

During a flow restoration procedure, the balloon guide catheter 76 can be moved through the vasculature towards a treatment area. A balloon 78, located on a distal end of the balloon guide catheter 76, can be expanded against the walls of a 80. The microcatheter 32 can be first be delivered through the balloon guide catheter 76. The self-expandable member 16 can be then be delivered through the microcatheter 32. Alternatively, the self-expanding member 16 can be delivered with the microcatheter 32. The self-expanding member 16 can be in a volume-reduced form within the microcatheter 32. The microcatheter 32 can be advanced through the vessel 80 and placed adjacent a thrombus 82. The self-expanding member 16 can be positioned such that the proximal portion 28 is upstream of the thrombus 82, the distal elements 38 are downstream of the thrombus, and the distal portion 30 of self-expanding member 16 is located radially adjacent to the thrombus 82. In a preferred arrangement, the microcatheter 32 can be placed alongside the thrombus 82 such that a distal tip 84 of the microcatheter 32 is beyond the thrombus 82, wherein the distal tip 84 is from greater than about 0 mm to about 10 mm or more, or about 3 mm to about 5 mm beyond the thrombus 82, though other ranges and values are also possible. In a preferred arrangement, the distal portion 30 of self-expanding member 16 can be positioned such that portions of distal portion 30 extend both proximally and distally of thrombus 82.

Figure 13:
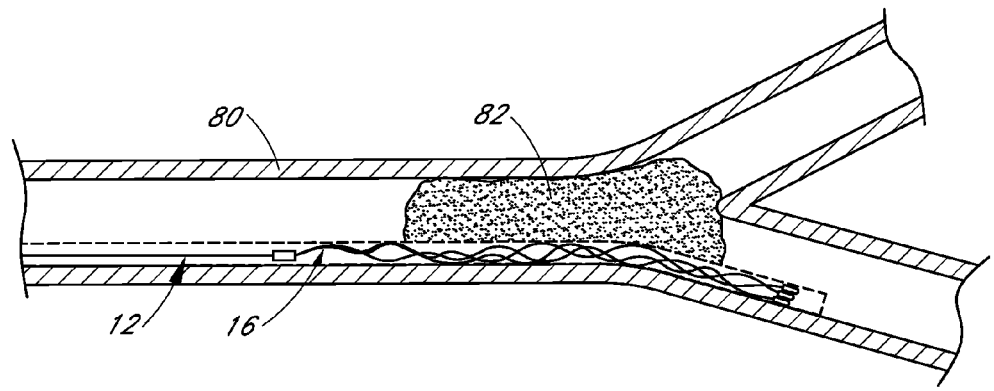

As illustrated in FIG. 13, the self-expanding member 16 can be held in a fixed position by holding the guidewire 12 stationary while the microcatheter 32 is withdrawn (i.e. pulled proximally). As the microcatheter is withdrawn, the self-expanding member 16 can be released from its volume-reduced form, and can expand. The self-expanding member 16 can assume at least a portion of its unconstrained form, thereby expanding to bring at least part of the distal portion 30, and its filaments 18 and cells 20, into penetrating contact with the thrombus 82. If the position of the self-expanding member 16 need to be adjusted, the guidewire 12 and/or microcatheter 32 can be moved together or individually, and if necessary, the self-expanding device 16 can be placed back in the microcatheter and then redeployed. The tapered proximal portion 28 can facilitate this type of repositioning.

Once deployed, the self-expanding member 16 can exert an outward radial force on the thrombus 82, as described above, thus reducing the cross-sectional area of the thrombus 82, forming a channel for immediately re-establishing at least partial blood flow through the blood vessel 80 past the thrombus 82, and/or loosening the thrombus from the vessel wall. In some embodiments, for example, about 10% to about 60% of the original thrombus 82 circumference can be separated from the vessel wall after the self-expanding member 16 is deployed, and the ability of the thrombus 82 to hang onto the vessel wall via adhesion and friction can accordingly reduced In some embodiments, the cross sectional area of the thrombus 82 can be significantly reduced by the deployed self-expanding member 16, resulting in a thrombus 82 having about 30% to about 95% of its original cross sectional area, but more typically about 50% to about 80% of its original cross sectional area In some embodiments, administration of an effective amount of a clot-busting drug, such as, for example tissue plasminogen activator (tPA), to the site of the thrombus 82 can further be applied during the blood flow restoration procedure to enhance dissolution of the thrombus 82. In some embodiments, the open channel created by the self-expanding member 16 can increase the exposed surface area of the thrombus 82, thereby facilitating faster dissolution of the thrombus 82 with such clot-busting drugs.

Immediately restoring at least partial blood flow with a self-expanding member 16 can provide a significant advantage over known apparatuses and methods for treating cerebral arteries occluded by thrombi because known apparatuses and methods may take hours to re-establish flow, and it is well established that the risk and degree of permanent neurological deficit increases rapidly with increased time from onset of symptoms to blood flow restoration. For example, immediate flow restoration can be advantageous in helping to maintain perforator patency. Thus, immediate flow restoration past the thrombus 82 can inhibit occlusion of perforator vessels nearby in the human body.

Additionally, vessels that are distal to an occluded area can often be deprived of blood flow and oxygen. Restoring blood flow in a gradual manner, through an immediate restoration of at least some partial blood flow, followed eventually by complete blood flow, can help inhibit reperfusion injury to vessels distal of the thrombus (i.e. injury caused by sudden, complete restoration of blood flow). Initial expansion of the self-expanding member 16 can allow the vessel to have some time to react and adapt to the changes to blood flow, pressure, stresses, and strains, and can allow the vessel to be conditioned to the onset of changes.

Figure 14:
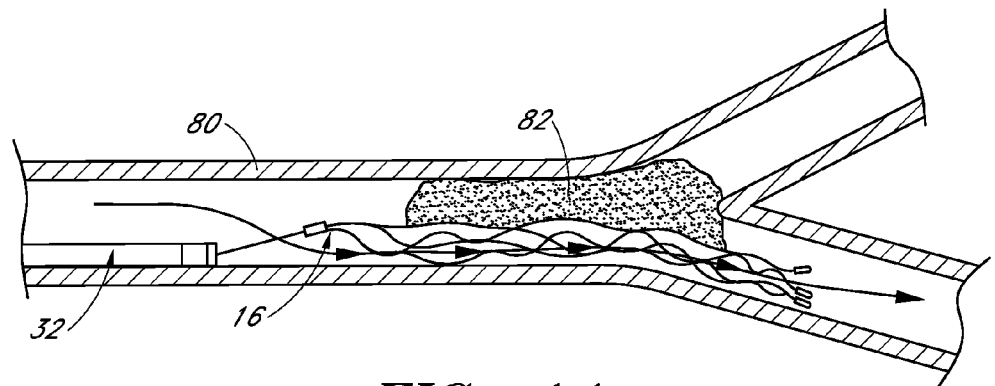
Figure 15:
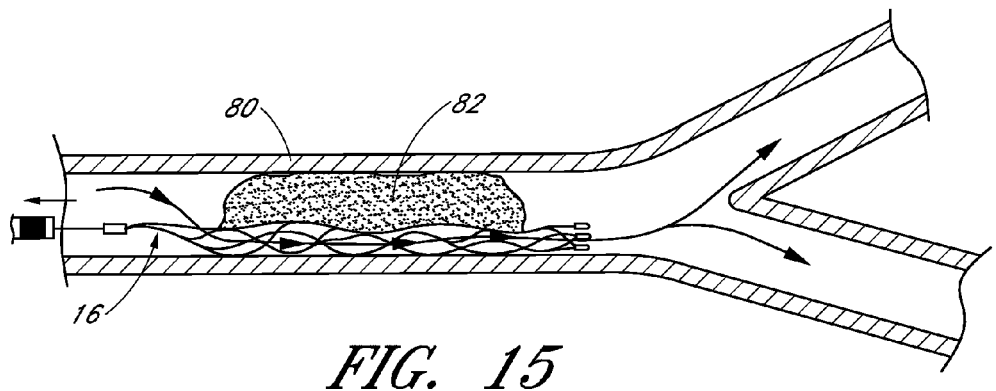

With continued reference to FIGS. 14 and 15, once the self-expanding member 16 has engaged and captured the thrombus 82, the thrombus 82 can be removed. Prior to pulling back on the guidewire 12, the microcatheter 32 can be manipulated. For example, the microcatheter 32 can be moved forward to a predetermined point relative to the self-expanding member 16. Use of markers along the microcatheter 32 and/or self-expanding member 16 can be used to determine the relative locations of the microcatheter 32 and self-expanding member 16. For example, the microcatheter 32 can be moved distally until it covers a marker on the proximal portion 28 or connection mechanism 14 (e.g. sleeve 48). The microcatheter 32 and self-expanding member 16 can then be removed together. Description of the use of such markers can be found, for example, in PCT Publication No. WO 2009/105710, which is incorporated by reference in its entirety.

As the thrombus 82 is removed, the distal elements 36 and/or the bent distal ends of the self-expanding member 16 can aid in gripping and/or pulling on the thrombus 82, thereby inhibiting slippage. Additionally, as the vessel size changes in diameter, the self-expanding member 16 can continuously adjust by expanding or contracting to accommodate vessel size. As the self-expanding member 16 expands or contracts, the cells 20 can generally maintain their same shape and size, as described above, thereby inhibiting unwanted slippage or dissection of the thrombus 82.

With reference to FIGS. 10 and 15, during retrieval of the device 10 and thrombus 82, the initial channel created for flow restoration through or past the thrombus 82 can remain open. The balloon 78 can remain inflated to provide for maximum proximal flow control. For example, in some embodiments the balloon 78 can ensure that there is no flow proximally through the vessel from the balloon 78 towards the self-expanding member 16 As part of the retrieval procedure, continuous aspiration can be employed through the balloon guide catheter 76 with vigorous aspiration when the self-expanding member 16 is near a distal tip 86 of the balloon guide catheter. For example, the balloon guide catheter 76 can include a syringe 88 for expanding the balloon 78, and a separate syringe 90 for aspiration. Aspiration assistance can enable flow reversal through the self-expanding member 16 and thrombus 82. The aspiration with flow reversal can help allow the distal vasculature to continue to have blood perfusing through the vessels during the retrieval process, and can inhibit the possibility of distal emboli. There can be an advantage to having blood flow across the self-expanding device 16 and thrombus 82 with the potential of natural lysing of blood and increased surface area for thrombus dissolving medicines, if they are provided. The aspiration with flow reversal can also assist in the thrombus retrieval process by aiding in the removal of the thrombus 82. The flow can be directed towards the lumen of the balloon guide catheter 76 due to the aspiration. The self-expanding member 16 and thrombus 82 can thus be assisted by the flow to enter the lumen of the balloon guide catheter 76. In some embodiments, if withdrawal into the balloon guide catheter 76 is difficult for any reason during aspiration, the balloon 78 can be deflated, and the balloon guide catheter 76, microcatheter 32, and device 10 as a unit can be withdrawn simultaneously while maintaining aspiration.

With reference to FIGS. 16A-C, the self-expanding member 16 can alternatively, or additionally, be used to assist in flow restoration across a bifurcation, bi-vessel, and/or multi-vessel. For example, the self-expanding member 16 illustrated in FIGS. 1, 9A and/or 9B can be used to help remove a thrombus 82 that is positioned at a bifurcation. In particular, in some embodiments the self-expanding member 16 of FIG. 1 can be strong enough itself to pull and retrieve the clot from the bifurcation area. In other embodiments the self-expanding member 16 illustrated in FIG. 9A or 9B can be used.

With reference to FIG. 17, and as described above, the device 10 can include a connection mechanism 14 that permits detachment of the self-expanding member 16. During a blood flow restoration procedure, the self-expanding member 16 is usually not detached. Rather, it remains connected to the guidewire 12, and can be pulled back with the microcatheter 32 along with the thrombus 82 into the balloon guide catheter 76. However, during some procedures a surgeon or other medical personnel may determine that it is necessary or advantageous to detach the self-expanding member 16. For example, after deployment of the self-expanding member 16, the self-expanding member 16 can initiate at least partial flow restoration as described above. Depending on a patient's particular anatomy and/or physical condition, the surgeon or other medical personnel may determine that it is safer to leave the self-expanding member 16 behind after deployment rather than attempt to continue to pull the thrombus 82 through the vasculature and into the microcatheter 32 or balloon guide catheter 76. Alternatively, the surgeon may determine that further withdrawal of the thrombus 82 may result in slippage, or loss of the thrombus 82 back into the vasculature. In these or other similar circumstances, a connection mechanism 14 that permits detachment can advantageously be used to detach the self-expanding member 16.

Additionally, and as described above, the device 10 can be used as a device for use as an implantable member (e.g. stent). For example, the guidewire 12, connection mechanism 14, and self-expanding member 16 can be delivered through a microcatheter 32 to a treatment site such as a stenosis or aneurysm. Similar to the method described above, the microcatheter can be withdrawn, and the self-expanding member 16 can expand against a vessel wall. Similar to use as a flow restoration device, if necessary the self-expanding member 16 can be repositioned if it is not placed correctly on a first attempt. Once the self-expanding member 16 is in a desired location at the treatment site, the self-expanding member 16 can then be detached from the guidewire 12 and be used as an implantable member.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments can be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A medical device comprising:
  a guidewire having a proximal end and a distal end, the distal end comprising a stem;
  a connection mechanism comprising (a) the stem, (b) a ball attached directly to the stem, (c) a keyway structure configured to receive the stem and the ball, (d) a sleeve surrounding the keyway structure, the stem, and the ball, and (e) an adhesive between (i) the sleeve and (ii) the stem and the ball, the stem and the ball positioned in the keyway, and the ball being unreleasable from the keyway and the sleeve; and
  a self-expanding member attached to the distal end of the guidewire via the connection mechanism, the self-expanding member having a mesh configuration and comprising:
    the keyway structure,
    a proximal portion having a first plurality of cells, the proximal portion being tapered along a longitudinal portion of its length;
    a distal portion having a second plurality of cells, the distal portion forming a generally tube-like configuration having a central, longitudinal axis; and
    a seam along a longitudinal axis of the distal portion, the seam forming two edges extending generally longitudinally along the self-expanding member;
    wherein the self-expanding member can be modified into a volume-reduced form having a generally coiled, tubular configuration for insertion within a microcatheter, the edges of the distal portion being overlapped in the volume-reduced, coiled configuration such that in the volume-reduced, coiled configuration the self-expanding member has multiple layers in at least one radial direction;

wherein a distal end of the distal portion further comprises filaments that include distal elements, the filaments and distal elements of the distal end being bent radially inwardly towards the central longitudinal axis;

wherein the first plurality of cells comprises filaments having a filament thickness of between 0.045 mm and 0.080 mm, and a filament width of between 0.040 mm and 0.090 mm;

wherein the second plurality of cells comprises filaments having a filament thickness of between 0.040 mm and 0.075 mm, and a filament width of between 0.038 mm and 0.082 mm;

wherein the second plurality of cells comprises cells having a width of between 3.50 mm to 5.50 mm and a height of between 2.50 mm to 4.5 mm;

wherein the self-expanding member has a radial force measurement greater than or equal to 0.0010 N/mm and a chronic outward force of less than or equal to 0.026 N/mm as measured using a thin film method of testing, and a radial force measurement of between approximately 6 to 37 gf/in as measured using a two-pin method of testing.

2. The medical device of claim 1, wherein the connection mechanism comprises a detachable mechanism for detaching the self-expanding member from the guidewire.

3. The medical device of claim 2, wherein the detachable mechanism comprises an electrolytically severable joint.

4. The medical device of claim 1, wherein the self-expanding member has a dislodgment force that ranges between 0.010 N and 0.700 N, the dislodgment force being measured by determining the force required to cause a fully deployed self-expanding member to slip axially along an in vitro model simulating an artery by pulling the self-expanding member along a specified length and recording the force at which slippage occurs.

5. The medical device of claim 1, wherein the self-expanding member has a total filament length and wherein the self-expanding member is configured to engage and remove thrombi of a particular range of length such that a ratio of the total filament length of the self-expanding member to the thrombus length in the particular range is between 10 to 15.

6. The medical device of claim 5, wherein the self-expanding member has a total filament length of 255 mm, a ratio of 12.75, and is configured to engage and remove thrombi that range up to approximately 20 mm in length.

7. The medical device of claim 1, wherein the second plurality of cells comprises filaments that have an average thickness of between 0.048 mm and 0.067 mm, and an average width of between 0.053 mm and 0.067 mm.

8. A medical device comprising:
a guidewire having a proximal end and a distal end;
a self-expanding member attached to the distal end of the guidewire, the self-expanding member having a mesh configuration and comprising:
a proximal portion comprising a single piece forming (a) a first plurality of cells and (b) a part configured to receive at least one of (i) the distal end of the guidewire or (ii) a ball attached directly to the distal end of the guidewire, the proximal portion being tapered along a longitudinal portion of its length;
a distal portion having a second plurality of cells, the distal portion forming a generally tube-like configuration having a central, longitudinal axis; and
a seam along a longitudinal axis of the distal portion, the seam forming two edges extending generally longitudinally along the self-expanding member;
wherein the self-expanding member can be modified into a volume- reduced form having a generally coiled, tubular configuration for insertion within a microcatheter, the edges of the distal portion being overlapped in the volume- reduced, coiled configuration such that in the volume-reduced, coiled configuration the self-expanding member has multiple layers in at least one radial direction;
wherein a distal end of the distal portion further comprises filaments that include a plurality of distal elements, the filaments of the distal end being bent radially inwardly towards the central longitudinal axis;
a sleeve surrounding (a) the part configured to receive at least one of (i) the distal end of the guidewire or (ii) a ball attached to the distal end of the guidewire, and (b) the at least one of the distal end of the guidewire or the ball; and
an adhesive between (i) the sleeve and (ii) the at least one of the distal end of the guidewire or the ball;
and wherein the at least one of (i) the distal end of the guidewire or (ii) the ball is positioned in the part of the single piece of the proximal portion; and
wherein the at least one of (i) the distal end of the guidewire or (ii) the ball is unreleasable from the sleeve and the part of the single piece of the proximal portion.

9. The medical device of claim 8, wherein the distal elements comprise marker bands.

10. The medical device of claim 8, wherein the distal elements have a hook-like configuration configured to aid in thrombus retention.

11. The medical device of claim 8, wherein the filaments of the distal end are bent radially inwardly at an angle between approximately ten to thirty degrees.

12. A medical device comprising:
a guidewire having a proximal end and a distal end;
a connection mechanism comprising (a) the distal end of the guidewire, (b) at least one of a slit or an opening, (c) a sleeve surrounding (i) the at least one of a slit or an opening and (ii) the distal end of the guidewire, and (d) an adhesive between the sleeve and the distal end of the guidewire, wherein the distal end of the guidewire is positioned in the at least one of a slit or an opening, and the distal end of the guidewire is unreleasable from the sleeve and the at least one of a slit or an opening; and
a self-expanding member attached to the distal end of the guidewire via the connection mechanism, the self-expanding member having a mesh configuration and comprising:
a proximal portion comprising a single component having (a) a first plurality of cells and (b) the at least one of a slit or an opening, the proximal portion being tapered along a longitudinal portion of its length;
a distal portion having a second plurality of cells, the distal portion forming a generally tube-like configuration having a central, longitudinal axis; and
a seam along a longitudinal axis of the distal portion, the seam forming two edges extending generally longitudinally along the self-expanding member;
wherein the self-expanding member can be modified into a volume- reduced form having a generally coiled, tubular configuration for insertion within a microcatheter, the edges of the distal portion being overlapped in the volume-reduced, coiled configuration such that in the volume-reduced, coiled configuration the self-expanding member has multiple layers in at least one radial direction;

wherein the first plurality of cells comprises filaments having a filament thickness of between 0.045 mm and 0.080 mm, and a filament width of between 0.040 mm and 0.090 mm;

wherein the second plurality of cells comprises filaments having a filament thickness of between 0.040 mm and 0.075 mm, and a filament width of between 0.038 mm and 0.082 mm.

13. The medical device of claim 12, wherein the second plurality of cells comprises cells having a width of between 3.50 mm to 5.50 mm and a height of between 2.50mm to 4.5 mm.

14. The medical device of claim 12, wherein the connection mechanism comprises an electrolytically severable region for detaching the self-expanding member from the guidewire.

15. A medical device comprising:
a guidewire having a proximal end and a distal end;
a ball attached directly to the distal end of the guidewire; and
a self-expanding member attached to the distal end of the guidewire, the self-expanding member having a mesh configuration and comprising:
a proximal portion having a first plurality of cells, the proximal portion being tapered along a longitudinal portion of its length, the proximal portion comprising an opening receiving the ball;
a distal portion having a second plurality of cells, the distal portion forming a generally tube-like configuration having a central, longitudinal axis; and
a seam along a longitudinal axis of the distal portion, the seam forming two edges extending generally longitudinally along the self-expanding member;
wherein the self-expanding member can be modified into a volume-reduced form having a generally coiled, tubular configuration for insertion within a microcatheter, the edges of the distal portion being overlapped in the volume-reduced, coiled configuration such that in the volume-reduced, coiled configuration the self-expanding member has multiple layers in at least one radial direction;
wherein the self-expanding member has a radial force measurement greater than or equal to 0.0010 N/mm and a chronic outward force of less than or equal to 0.026 N/mm as measured using a thin film method of testing, and a radial force measurement of between approximately 6 to 37 gf/in as measured using a two-pin method of testing;
a sleeve surrounding the ball and the opening of the proximal portion of the self-expanding member; and
an adhesive between the sleeve and the ball; and
wherein the ball is unreleasable from the sleeve and the opening of the proximal portion.

16. The medical device of claim 15, further comprising a detachable mechanism for detaching the self-expanding member from the guidewire.

17. A method of blood flow restoration in the neurovasculature comprising:
inserting a balloon guide catheter into the neurovasculature;
inflating a balloon on a distal end of the balloon guide catheter;
inserting a microcatheter through the distal end of the balloon guide catheter;
inserting the medical device of claim 1 into the microcatheter such that the distal portion of the self-expanding member is located adjacent a thrombus in the neurovasculature;
withdrawing the microcatheter so as to expose and deploy the self-expanding member, the self-expanding member configured to expand against the length of the thrombus and engage the thrombus;
retrieving the thrombus by moving the microcatheter until the microcatheter covers a portion of the self-expanding device, and then withdrawing both the microcatheter and self-expanding member together proximally; and
providing aspiration through the balloon guide catheter to assist in removing the thrombus.

18. The method of claim 17, wherein at least partial blood flow restoration is restored immediately upon engagement of the self-expanding device with the thrombus.

19. The method of claim 17, further comprising withdrawing the thrombus at least partially into the microcatheter.

20. The method of claim 17, further comprising withdrawing the thrombus at least partially into the balloon guide catheter.

21. The method of claim 17, wherein the connection mechanism comprises an electrolytically severable joint, and wherein the method of blood flow restoration further comprises detaching the self-expanding member from the guidewire.

22. The method of claim 17, further comprising repositioning the self-expanding member prior to retrieving the thrombus.

23. A method of implanting a medical device in the neurovasculature comprising:
inserting a guide catheter into the neurovasculature;
inserting a microcatheter through the distal end of the guide catheter;
inserting the medical device of claim 1 through the microcatheter such that the distal portion of the self-expanding member is located adjacent a treatment site in the neurovasculature;
withdrawing the microcatheter so as to expose and deploy the self-expanding device, the self-expanding device configured to expand against and engage the treatment site;
detaching the self-expanding member via electrolytic disintegration of a portion of the connection mechanism.

24. The method of claim 23, wherein the treatment site comprises a stenosis.

25. The method of claim 23, wherein the treatment site comprises an aneurysm.

26. The method of claim 23, further comprising repositioning the self-expanding member prior to detachment.

27. The medical device of claim 1, further comprising an insulative coating on the stem and the ball.

28. The medical device of claim 1, wherein the keyway structure is monolithic with the self-expanding member.

29. The medical device of claim 8, further comprising an insulative coating on at least one of the ball or the distal end of the guidewire.

30. The medical device of claim 8, wherein the sleeve comprises platinum.

31. The medical device of claim 12, further comprising an insulative coating on the distal end of the guidewire.

32. The medical device of claim 15, further comprising an insulative coating on at least one of the ball or the distal end of the guidewire.

* * * * *